(12) United States Patent
Sutton

(10) Patent No.: US 7,714,002 B2
(45) Date of Patent: May 11, 2010

(54) CARBOCYCLE AND HETEROCYCLE ANTAGONISTS OF P2Y$_1$ RECEPTOR USEFUL IN THE TREATMENT OF THROMBOTIC CONDITIONS

(75) Inventor: James C. Sutton, Pleasanton, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 989 days.

(21) Appl. No.: 11/474,841

(22) Filed: Jun. 26, 2006

(65) Prior Publication Data

US 2006/0293522 A1     Dec. 28, 2006

Related U.S. Application Data

(60) Provisional application No. 60/694,605, filed on Jun. 27, 2005.

(51) Int. Cl.
| A61K 31/44 | (2006.01) |
| C07D 213/69 | (2006.01) |
| C07D 213/74 | (2006.01) |

(52) U.S. Cl. ............. 514/349; 514/348; 546/296; 546/297

(58) Field of Classification Search ............ 546/296, 546/297; 514/348, 349
See application file for complete search history.

(56) References Cited

U.S. PATENT DOCUMENTS

| 3,118,888 A | 1/1964 | Giraldi et al. |
| 3,162,644 A | 12/1964 | Englisch et al. |
| 4,179,563 A | 12/1979 | Butler |
| 4,186,199 A | 1/1980 | Glamkowski et al. |
| 4,435,391 A | 3/1984 | Sasahara et al. |
| 4,663,453 A | 5/1987 | Glamkowski et al. |
| 4,840,947 A | 6/1989 | Glamkowski et al. |
| 4,886,822 A | 12/1989 | Shibuya et al. |
| 5,500,424 A | 3/1996 | Nagamine et al. |
| 5,547,966 A | 8/1996 | Atwal et al. |
| 5,612,359 A | 3/1997 | Murugesan |
| 5,708,008 A | 1/1998 | Audia et al. |
| 5,886,004 A | 3/1999 | Audia et al. |
| 6,020,357 A | 2/2000 | Pinto et al. |
| 6,043,265 A | 3/2000 | Murugesan et al. |
| 6,143,764 A | 11/2000 | Kubo et al. |
| 6,180,675 B1 | 1/2001 | Widdowson et al. |
| 6,187,797 B1 | 2/2001 | Pruitt et al. |
| 6,329,395 B1 | 12/2001 | Dugar et al. |
| 6,586,453 B2 | 7/2003 | Dhanoa et al. |
| 6,596,746 B1 | 7/2003 | Das et al. |
| 6,656,933 B2 | 12/2003 | Hickey |
| 6,825,355 B2 | 11/2004 | Das et al. |
| 6,863,647 B2 | 3/2005 | Pevarello et al. |
| 2002/0077486 A1 | 6/2002 | Scarborough et al. |
| 2003/0061667 A1 | 4/2003 | Lim et al. |
| 2003/0065176 A1 | 4/2003 | Kang et al. |
| 2003/0153568 A1 | 8/2003 | Cusack et al. |
| 2003/0195232 A1 | 10/2003 | Kawasaki et al. |
| 2003/0207870 A1 | 11/2003 | Dumas et al. |
| 2003/0216396 A1 | 11/2003 | Dumas et al. |
| 2004/0023961 A1 | 2/2004 | Dumas et al. |
| 2004/0038992 A1 | 2/2004 | Bemis et al. |
| 2004/0102636 A1 | 5/2004 | Miller et al. |
| 2004/0209930 A1 | 10/2004 | Carboni et al. |
| 2004/0259875 A1 | 12/2004 | Yura et al. |
| 2005/0009815 A1 | 1/2005 | DeVita et al. |
| 2005/0012254 A1 | 1/2005 | Hsu |
| 2005/0119304 A1 | 6/2005 | Yura et al. |
| 2005/0203146 A1 | 9/2005 | Herpin et al. |
| 2005/0256161 A1 | 11/2005 | Tempest et al. |
| 2005/0261244 A1 | 11/2005 | Tuerdi et al. |
| 2005/0267119 A1 | 12/2005 | Chao et al. |
| 2006/0173002 A1 | 8/2006 | Sutton et al. |
| 2006/0293281 A1 | 12/2006 | Qiao et al. |
| 2006/0293336 A1 | 12/2006 | Sutton et al. |
| 2006/0293522 A1 | 12/2006 | Sutton |
| 2007/0004677 A1 | 1/2007 | Chao et al. |

FOREIGN PATENT DOCUMENTS

| EP | 0 028 489 | 5/1981 |
| EP | 0 129 692 | 1/1985 |
| EP | 0 265 734 | 5/1988 |
| EP | 0 286 979 | 10/1988 |
| EP | 0 638 557 | 2/1995 |
| EP | 1 123 918 | 8/2001 |
| EP | 1120409 | 8/2001 |
| EP | 1 402 888 | 3/2004 |

(Continued)

OTHER PUBLICATIONS

U.S. Appl. No. 11/872,816, filed Oct. 16, 2007, Lam et al.

(Continued)

*Primary Examiner*—Patricia L Morris
(74) *Attorney, Agent, or Firm*—Jing G. Sun

(57) ABSTRACT

The present invention provides novel urea mimics and analogues of Formula (I):

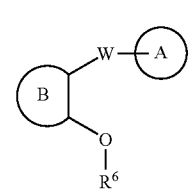

or a stereoisomer, tautomer, pharmaceutically acceptable salt or solvate form thereof, wherein the variables A, B, W, and $R^6$ are as defined herein. These compounds are selective inhibitors of the human P2Y$_1$ receptor which can be used as medicaments.

6 Claims, No Drawings

FOREIGN PATENT DOCUMENTS

| | | |
|---|---|---|
| EP | 1 661 879 | 5/2006 |
| EP | 1 712 242 | 10/2006 |
| FR | 1 342 550 | 12/1962 |
| JP | 56-167649 | 12/1981 |
| JP | 62-280847 | 12/1987 |
| JP | 3-39740 | 2/1991 |
| JP | 4-319958 | 11/1992 |
| JP | 7-101153 | 4/1995 |
| JP | 2001-89412 | 4/2001 |
| WO | WO 96/17825 | 6/1996 |
| WO | WO 97/29743 | 8/1997 |
| WO | WO 98/18430 | 5/1998 |
| WO | WO 98/37035 | 8/1998 |
| WO | WO 98/57951 | 12/1998 |
| WO | WO 99/31086 | 6/1999 |
| WO | WO 99/32463 | 7/1999 |
| WO | WO 00/01389 | 1/2000 |
| WO | WO 00/59506 | 10/2000 |
| WO | WO 00/76495 | 12/2000 |
| WO | WO 00/76970 | 12/2000 |
| WO | WO 01/23358 | 4/2001 |
| WO | WO 01/40231 | 6/2001 |
| WO | WO 01/47919 | 7/2001 |
| WO | WO 01/51490 | 7/2001 |
| WO | WO 01/55146 | 8/2001 |
| WO | WO 01/57008 | 8/2001 |
| WO | WO 01/72751 | 10/2001 |
| WO | WO 02/44145 | 6/2002 |
| WO | WO 02/064211 | 8/2002 |
| WO | WO 02/088090 | 11/2002 |
| WO | WO02/090352 A2 | 11/2002 |
| WO | WO 03/007955 | 1/2003 |
| WO | WO 03/013517 | 2/2003 |
| WO | WO 03/014064 | 2/2003 |
| WO | WO 03/026652 | 4/2003 |
| WO | WO 03/045920 | 6/2003 |
| WO | WO 03/055484 | 7/2003 |
| WO | WO 03/055848 | 7/2003 |
| WO | WO 03/080553 | 10/2003 |
| WO | WO 2004/002481 | 1/2004 |
| WO | WO 2004/012733 | 2/2004 |
| WO | WO 2004/022529 | 3/2004 |
| WO | WO 2004/046090 | 6/2004 |
| WO | WO 2004/060907 | 7/2004 |
| WO | WO 2004/085433 | 10/2004 |
| WO | WO 2004/110374 | 12/2004 |
| WO | WO2005/037763 A | 4/2005 |
| WO | WO 2005/042488 | 5/2005 |
| WO | WO 2005/063293 | 7/2005 |
| WO | WO2005/070920 A | 8/2005 |
| WO | WO 2006/091963 | 8/2006 |

OTHER PUBLICATIONS

Atwal, K.S. et al., "Cardioselective Antiischemic ATP-Sensitive Potassium Channel Openers. 4. Structure-Activity Studies on Benzopyranylcyanoguanidines: Replacement of the Benzopyran Portion", Journal of Medicinal Chemistry, vol. 39, No. 1, pp. 304-313 (1996).

Bareich, D.C. et al., "Simultaneous In Vitro Assay of the First Four Enzymes in the Fungal Aspartate Pathway Identifies a New Class of Aspartate Kinase Inhibitor", Chemistry & Biology, vol. 10, pp. 967-973 (2003).

Beaver, D.J. et al., "The Preparation and Bacteriostatic Activity of Substituted Ureas", J. Am. Chem. Soc., vol. 79, pp. 1236-1245 (1957).

Bensemann, I. et al., "Creation of hydrogen bonded 1D networks by co-crystallization of N,N'-bis(2-pyridyl)aryldiamines with dicarboxylic acids", Org. Biomol. Chem., vol. 1, pp. 1425-1434 (2003).

Bundgaard, H., Chapter 5: "Design and Application of Prodrugs", A Textbook of Drug Design and Development, Harwood Academic Publishers, publ., Krogsgaard-Larsen, P. et al., eds., pp. 113-191 (1991).

Bundgaard, H., "Prodrugs as a means to improve the delivery of peptide drugs", Advanced Drug Delivery Reviews, vol. 8, pp. 1-38 (1992).

Chan, D.M.T. et al., Chapter 5: "Recent Advances in Copper-promoted C-Heteroatom Bond Cross-coupling Reactions with Boronic Acids and Derivatives", Boronic Acids: Preparation and Applications in Organic Synthesis and Medicine, Wiley-VCH Verlag GmbH & Co., publ., Hall, D.G., ed., pp. 205-240 (2005).

Chou, T.-C. et al., "Quantitative Analysis of Dose-Effect Relationships: The Combined Effects of Multiple Drugs or Enzyme Inhibitors", Adv. Enzyme Regul., vol. 22, pp. 27-55 (1984).

Cobern, D. et al., "Some New p-Chlorophenoxycarbanilides and Their Bacteriostatic Activities", J. Med. Chem., vol. 11, pp. 163-164 (1968).

Duncan, Jr., R.L. et al., "Synthesis of Indolo- and Benzimidazoquinazolines and Benzodiazepines", Journal of Heterocyclic Chemistry, vol. 10, pp. 65-70 (1973).

Gallou, I. et al., "Practical Synthesis of Unsymmetrical Ureas from Isopropenyl Carbamates", J. Org. Chem., vol. 70, No. 17, pp. 6960-6963 (2005).

Glamkowski, E.J. et al., "Synthesis of 1,2-Dihydroindolo[1,7-ab][1,5]benzodiazepines and Related Structures (1). A New Heterocyclic Ring System", J. Heterocyclic Chem., vol. 16, pp. 865-869 (1979).

Glamkowski, E.J. et al., "Tetracyclic Benzodiazepines. 3. Synthesis of the 2,3-Dihydro-1H-quino[1,8-ab][1,5]benzodiazepine Ring System, and Derivatives of Potential Biological Interest", J. Heterocyclic Chem., vol. 24, pp. 733-737 (1987).

Gramatica, P. et al., "QSAR approach for the selection of congeneric compounds with a similar toxicological mode of action", Chemosphere, vol. 42, pp. 873-883 (2001).

Gschwend, D.A. et al., "Specificity in Structure-Based Drug Design: Identification of a Novel, Selective Inhibitor of Pneumocystis carinii Dihydrofolate Reductase", Proteins: Structure, Function and Genetics, vol. 29, pp. 59-67 (1997).

Hai, P.V. et al., "p-Cyclopentylacetophenone and Its Derivatives", J. Org. Chem., vol. 23, pp. 39-42 (1958).

Hamada, Y. et al., "The antimicrobial activity and syntheses of carbanilide derivatives," Yakugaku Zasshi, vol. 96, No. 5, pp. 663-668 (1976) (English abstract).

Herr, R.J., "Product Class 5: Seven-Membered Hetarenes with Two or More Heteroatoms", Science of Synthesis, vol. 17, pp. 929-977 (2004).

Ito, Y. et al., "Syntheses of Nitrogen-containing Heterocyclic Compounds. XXIX. An Improved Method for the Preparation of 10H-Pyrido[3,2-b][1,4]benzoxazine (1-Azaphenoxazine)", Chem. Pharm. Bull., vol. 26, No. 5, pp. 1375-1383 (1978).

Janssens, R. et al., "Cloning and Tissue Distribution of the Human P2Y$_1$ Receptor", Biochemical and Biophysical Research Communications, vol. 221, No. 3, pp. 588-593 (1996).

Kakeya, N. et al., "Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid", Chem. Pharm. Bull., vol. 32, No. 2, pp. 692-698 (1984).

Kane, Jr., J.L. et al., "Ureas of 5-Aminopyrazole and 2-Aminothiazole Inhibit Growth of Gram-Positive Bacteria", Bioorganic & Medicinal Chemistry Letters, vol. 13, pp. 4463-4466 (2003).

Lane, B.S. et al., "Direct Palladium-Catalyzed C-2 and C-3 Arylation of Indoles: A Mechanistic Rationale for Regioselectivity", J. Am. Chem. Soc., vol. 127, No. 22, pp. 8050-8057 (2005).

Ley, S.V. et al., "Modern Synthetic Methods for Copper-Mediated C(aryl)-O, C(aryl)-N, and C(aryl)-S Bond Formation", Angewandte Chemie Int. Ed., vol. 42, pp. 5400-5449 (2003).

Marcincal-Lefebvre, A. et al., "2-[2-(Phenylthio)phenylamino]nicotinic acids and 2-[4-(phenylthio)phenylamino]nicotinic acids. Synthesis and antiinflammatory activity", Annales Pharmaceutiques Francaises, vol. 38, No. 3, pp. 243-252 (1980) (English abstract).

Matsuo, M. et al., "New 2-Aryliminoimidazolidines. I. Synthesis and Antihypertensive Properties of 2-(2-Phenoxyphenylimino)imidazolidines and Related Compounds", Chem. Pharm. Bull., vol. 33, No. 10, pp. 4409-4421 (1985).

Nielsen, N.M. et al., "Glycolamide Esters as Biolabile Prodrugs of Carboxylic Acid Agents: Synthesis, Stability, Bioconversion, and Physicochemical Properties", Journal of Pharmaceutical Sciences, vol. 77, No. 4, pp. 285-298 (1988).

Peng, C.-T. et al., "The Synthesis of Some 6-N-Substituted Amido Derivatives of 4,6-Diaminoquinaldine and a Study of their in vitro Antibacterial Activity", J. Am. Chem. Soc., vol. 78, pp. 3703-3708 (1956).

Phillips, G. et al., "Design, Synthesis, and Activity of 2,6-Diphenoxypyridine-Derived Factor Xa Inhibitors", J. Med. Chem., vol. 42, No. 10, pp. 1749-1756 (1999).

Rajanarendar, E. et al., "Synthesis of isoxazolylpyrazolo[3,4-d]thiazoles and isoxazolylthiazoles and their antibacterial and antifungal activity", Indian Journal of Chemistry, vol. 43B, pp. 168-173 (2004).

Roberts, M.E. et al., "On the Alkyl Derivatives of the Isomeric Ortho and Para-phenoxyphenyl Thiazolidones", The University of Kansas Science Bulletin, vol. 25, No. 11, pp. 213-227 (1938).

Rodig, O.R. et al., "Pyridine Chemistry. II. Further Studies on the Smiles Rearrangement of the 3-Amino-2,2'-dipyridyl Sulfide System. The Synthesis of Some 1,6-Diazaphenothiazines", Journal of Medicinal Chemistry, vol. 9, pp. 116-120 (1966).

Still, W.C. et al., "Rapid Chromatographic Technique for Preparative Separations with Moderate Resolution", J. Org. Chem., vol. 43, No. 14, pp. 2923-2925 (1978).

Takeuchi, I. et al., "On the antimicrobial activity and syntheses of carbanilide and salicylanilide derivatives", Yakugaku Zasshi, vol. 102, No. 11, pp. 1023-1030 (1982) (English abstract).

Taylor, Jr., E.C. et al., "Pteridines. XIV. Further Studies on a New Approach to Pteridine Synthesis", J. Am. Chem. Soc., vol. 78, pp. 210-213 (1956).

Tomita, M. et al., "Synthesis of thiazole derivatives containing diphenyl ether nucleus", Yakugaku Zasshi, vol. 75, pp. 1077-1081 (1955) (English abstract).

Widder, K.J. et al., eds., Section III: "Prodrugs", Methods in Enzymology, vol. 112, Academic Press, Inc., publ., pp. 309-396 (1985).

Wisterowicz, K. et al., "Studies on Pyrazine Derivatives. XXVI. Synthesis and tuberculostatic activity of N-pyrazinylthioureas", Acta Polon. Pharm., vol. 46, No. 2, pp. 101-113 (1989).

Wong, P.C. et al., "Nonpeptide Factor Xa Inhibitors: I. Studies with SF303 and SK549, a New Class of Potent Antithrombotics", The Journal of Pharmacology and Experimental Therapeutics, vol. 292, No. 1, pp. 351-357 (2000).

Wong, P.C. et al., "Nonpeptide Factor Xa Inhibitors II. Antithrombotic Evaluation in a Rabbit Model of Electrically Induced Carotid Artery Thrombosis", The Journal of Pharmacology and Experimental Therapeutics, vol. 295, No. 1, pp. 212-218 (2000).

Woźniak, K. et al., "Structural Similarities and Differences between N-Phenylureas and N-Phenylthioureas", J. Phys. Chem., vol. 99, No. 21, pp. 8888-8895 (1995).

Boeynaems et al, "Overview of P2Y Receptors as Therapeutic Targets", *Drug Development Research* 52:187-189 (2001).

Burnstock et al, "P2 Purinergic Receptors: Modulation of Cell Function and Therapeutic Potential", *The Journal of Pharmacology and Experimental Therapeutics*, vol. 295, 862-869, 2000.

Abbracchio et al., "Purinoceptors: Are There Families of P2X and P2Y Purinoceptors?", *Pharmac. Ther.*, vol. 64, pp. 445-475, 1994.

Abbracchio et al., "Characterization of the UDP-glucose receptor (re-named here the $P2Y_{14}$ receptor) adds diversity to the P2Y receptor family", *Trends in Pharmacological Sciences*, vol. 24, No. 2, Feb. 2003.

Norenberg et al., "Characterization and possible function of adenosine 5'-triphosphate receptors in activated rat microglia", *Br. J. Pharmacol,*, (1994), 111, 942-950.

Salter et al., ATP Causes Release of Intracellular $Ca^{2+}$ via the Phospholipase $C\beta/IP_3$ Pathway in Astrocytes from the Dorsal Spinal Cord, *The Journal of Neuroscience*, Apr. 1995, 15(4): 2961-2971.

Jin et al., Coactivaton of two different G protein-coupled receptors is essential for ADP-induced platelet aggregation, *Proc. Natl. Acad. Sci. USA*, vol. 95, pp. 8070-8074, Jul. 1998.

Jin et al., "Molecular Basis for ADP-induced Platelet Activation", *The Journal of Biological Chemistry*, vol. 273, No. 4, pp. 2030-2034, 1998.

Savi et al., "Role of P2Y1 purinoceptor in ADP-induced platelet activation", *FEBS Letters* 422 (1998), 291-295.

Hechler et al., "The $P2Y_1$ receptor, necessary but not sufficient to support full ADP-induced platelet aggregation, is not the target of the drug clopidogrel", *British Journal of Haematology*, 1998, 103, 858-866.

Leon et al., "Key Role of the $P2Y_1$ Receptor in Tissue Factor-Induced Thrombin-Dependent Acute Thromboembolism", *Circulation* 2001, 103, 718-723.

Daniel et al., "Molecular Basis for ADP-induced Platelet Activation", *The Journal of Biomedical Chemistry*, vol. 273, No. 4, pp. 2024-2029, 1998.

Lenain et al., "Inhibition of localized thrombosis in $P2Y_1$-deficient mice and rodents treated with MRS2179, a $P2Y_1$ receptor antagonist", *Journal of Thrombosis and Haemostatis*, 1, 1144-1149 (2003).

Fabre et al., "Decreased platelet aggregation, increased bleeding time and resistance to thromboembolism", *Nature Medicine*, vol. 5, No. 10, Oct. 1999.

Hechler et al., "MRS2500 [2-Iodo-$N^6$-methyl-(N)-methanocarba-2'-deoxyadenosine-3', 5'-biphosphate], a Potent, Selective, and Stable Antagonist of the Platelet $P2Y_1$ Receptor with Strong Antithrombotic Activity in Mice", *The Journal of Pharmacology and Experimental Therapeutics* 316:556-563, 2006.

Gachet et al., "The platelet P2 receptors in arterial thrombosis", *Blood Cells, Molecules & Diseases*, 36 (2006) 223-227.

CARBOCYCLE AND HETEROCYCLE ANTAGONISTS OF $P2Y_1$ RECEPTOR USEFUL IN THE TREATMENT OF THROMBOTIC CONDITIONS

CROSS-REFERENCE TO RELATED APPLICATIONS

The present application claims the priority benefit of U.S. Provisional Application No. 60/694,605, filed Jun. 27, 2005, which is expressly incorporated fully herein by reference.

FIELD OF THE INVENTION

The present invention provides novel carbocycle and heterocycle and analogues thereof, which are selective inhibitors of the human $P2Y_1$ receptor. The invention also provides for various pharmaceutical compositions of the same and methods for treating diseases responsive to modulation of $P2Y_1$ receptor activity.

BACKGROUND OF THE INVENTION

Purinoreceptors bind to and are activated by a variety of both ribosylated (nucleotide) and non-ribosylated (nucleoside) purines. This distinction has been used to classify these receptors into two broad groups: the P1 receptors (A1, A2a, A2b, and A3), which bind to and are activated by the nucleoside adenosine, and the P2 receptors, which comprise a second, more diverse class of receptors which are activated by a wide variety of nucleotides including ATP, ADP, UTP, and UDP. The P2 receptors can be further subdivided into two distinct types of receptors; the ionotropic P2X receptors that mediate cation flux across cellular membranes in response to ATP and the metabotropic P2Y family of receptors which are G-protein coupled receptors. In humans, the P2Y family of receptors is generally considered to consist of seven distantly related members; $P2Y_1$, $P2Y_2$, $P2Y_4$, $P2Y_6$, $P2Y_{11}$, $P2Y_{12}$, and $P2Y_{13}$ (Boeynaems, J. M. et al. *Drug Development Research* 2001, 52, 187-9). In addition, an eighth receptor, $P2Y_{14}$, has been considered by some to be a member of this class although it does not respond to ribosylated nucleotides and is activated by UDP-glucose (Abbracchio, M. P. et al. *Trends Pharmacol. Sci.* 2003, 24, 52-5).

Several studies have suggested that modulators of specific members of the P2Y family of receptors could have therapeutic potential for the treatment of a variety of disorders (for review, see Burnstock, G. and Williams, M. *J. Pharm. Exp Ther.* 2000, 295, 862-9), including diabetes, cancer, cystic fibrosis, and the treatment of ischemia-reperfusion injury (Abbracchio M. P. and Burnstock G. *Pharmacol. Ther.* 1994, 64, 445-475). $P2Y_1$ receptors, almost ubiquitous among human organs (Janssens, R. et al. *Biochem. Biophys. Res. Comm.* 1996, 221, 588-593) have been identified on microglia (Norenberg, W. et al. *Br. J. Pharmacol.* 1994, 111, 942-950) and on astrocytes (Salter M. W. and Hicks J. L. *J. Neurosc.* 1995, 15, 2961-2971). Extracellular ATP activates microglial and/or astrocytes via P2Y receptors and leads directly to the release of inflammatory mediators. Microglia and astrocytes are believed to play a role in the progression of Alzheimer's disease and other CNS inflammatory disorders such as stroke and multiple sclerosis.

Two members of the P2Y family, $P2Y_1$ and $P2Y_{12}$, are of particular interest as they have now both been shown to act as important receptors for ADP in platelets (Jin, J. et al. *Proc. Natl. Acad. Sci.* 1998, 95, 8070). ADP is a key activator of platelets and platelet activation is known to play a pivotal role in thrombus formation under conditions of high shear stress such as those found in the arterial circulation. In addition, more recent data has suggested that platelet activation may also play a role in mediating thrombus formation under lower shear stress such as that found in the venous circulation. ADP activates platelets by simultaneously interacting with both $P2Y_1$ and $P2Y_{12}$ to produce two separate intracellular signals which synergize together to produce complete platelet activation. (Jin, J. et al. *J. Biol. Chem.* 1998, 273, 2030-4). The first signal arises from ADP driven activation of the $P2Y_1$ receptor and can most easily be tracked by measuring the transitory increase in intracellular free $Ca^{+2}$. This signal appears to mediate the initial shape change reaction and to initiate the process of platelet activation. The second signal appears to be derived from ADP activation of the $P2Y_{12}$ receptor and serves to consolidate the process and produce an irreversible platelet aggregate. Using three structurally related but distinct inhibitors of $P2Y_1$ (A3P5P, A3P5PS, and A2P5P), Daniel, J. L. et al. (*J. Biol. Chem.* 1998, 273, 2024-9), Savi, P. et al. (*FEBS Letters* 1998, 422, 291-5), and Hechler, B. et al. (*Br. J. Haematol.* 1998, 103, 858-66) were the first to publish the observation that the inhibition of $P2Y_1$ activity alone could block ADP-driven aggregation independently of the $P2Y_{12}$ receptor. Although inhibition of platelet reactivity is often thought of as firm evidence of an antithrombotic activity, these antagonists lacked the necessary pharmacological properties for in vivo study. The first direct demonstration that inhibition of $P2Y_1$ activity could lead to an anti-thrombotic effect in vivo was reported by Leon, C. et al. *Circulation* 2001, 103, 718-23, in a model of thromboplastin induced thromboembolism using both a $P2Y_1$ knock-out mouse and the $P2Y_1$ antagonist MRS-2179 (Baurand, A. and Gachet, C. *Cardiovascular Drug Reviews* 2003, 21, 67-76). These results were subsequently extended to include the inhibition of both venous and arterial thrombosis in the rat (Lenain, N. et al. *J. Thromb. Haemost.* 2003, 1, 1144-9) and the confirmation of the phenotype of the $P2Y_1$ knock-out mouse in a second laboratory using an independently derived animal (Fabre, J-E. et al. *Nature Medicine* 1999, 5, 1199-1202). These studies highlighted the need for more potent and selective $P2Y_1$ antagonists and recently, using the $P2Y_1$ antagonist MRS-2500 (Hechler, B. et al. *J. Pharmacol Exp. Ther.* 2006, 316, 556-563) succeeded in demonstrating strong antithrombotic activity for a selective $P2Y_1$ antagonist in the mouse. Taken together, these data suggest that the discovery of novel $P2Y_1$ antagonists with improved pharmaceutical characteristics could have significant utility in the treatment of a variety of thrombotic or thromboembolic disorders (see Gachet, C. et al. *Blood Cell, Molecules and Disease* 2006, 36, 223-227 for a recent review).

SUMMARY OF THE INVENTION

Accordingly, the present invention provides novel carbocycle and heterocycle and analogues, which are useful as selective inhibitors of the $P2Y_1$ receptor including stereoisomers, tautomers, pharmaceutically acceptable salts, solvates, or prodrugs thereof.

The present invention also provides processes and intermediates for making the compounds of the present invention or a stereoisomer, tautomer, pharmaceutically acceptable salt, solvate, or prodrug thereof.

The present invention also provides pharmaceutical compositions comprising a pharmaceutically acceptable carrier and at least one of the compounds of the present invention or a stereoisomer, tautomer, pharmaceutically acceptable salt, solvate, or prodrug thereof.

The present invention also provides a method for modulation of platelet reactivity comprising administering to a host in need of such treatment a therapeutically effective amount of at least one of the compounds of the present invention or a stereoisomer, tautomer, pharmaceutically acceptable salt, solvate, or prodrug thereof.

The present invention also provides a method for treating thromboembolic disorders comprising administering to a host in need of such treatment a therapeutically effective amount of at least one of the compounds of the present invention or a stereoisomer, tautomer, pharmaceutically acceptable salt, solvate, or prodrug thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of a thrombotic or thromboembolic or other disorders.

These and other features of the invention will be set forth in the expanded form as the disclosure continues.

DETAILED DESCRIPTION OF PREFERRED EMBODIMENTS

In a first embodiment, the present invention provides, inter alia, a compound of Formula (I):

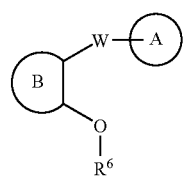

or a stereoisomer, tautomer, pharmaceutically acceptable salt, solvate, or prodrug thereof, wherein:

ring A is a carbocycle substituted with 0-4 $R^1$, wherein said carbocycle is selected from cyclohexyl, phenyl, indenyl, dihydroindenyl, naphthyl, dihydronaphthyl, and tetrahydronaphthyl;

ring B is a 5- to 6-membered heteroaryl comprising: carbon atoms and 1-4 ring heteroatoms selected from N, $NR^{11}$, N→O, $S(O)_p$, and O, wherein said heteroaryl is substituted with 0-4 $R^7$;

W is NH or O;

$R^1$ is, independently at each occurrence, =O, F, Cl, Br, I, $CF_3$, $-CF_2CF_3$, $OCF_3$, $-OCF_2CF_2H$, $-OCF_2CF_3$, $SiMe_3$, $-(CR^fR^f)_r-OR^c$, $SR^c$, CN, $NO_2$, $-(CR^fR^f)_r-NR^{12}R^{13}$, $-(CR^fR^f)_r-C(O)R^c$, $-(CR^fR^f)_r-CO_2R^c$, $-(CR^fR^f)_r-C(O)NR^{12}R^{13}$, $-OP(O)(OEt)_2$, 4,4,5,5-tetramethyl-1,3,2-dioxaborolanyl, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, $-(CR^fR^f)_r-C_{3-13}$ carbocycle substituted with 0-5 $R^b$, or $-(CR^fR^f)_r$-5- to 10-membered heterocycle comprising: carbon atoms and 1-4 heteroatoms selected from N, $NR^{11}$, O, and $S(O)_p$, wherein said heterocycle is substituted with 0-5 $R^b$;

alternatively, two $R^1$s on two adjacent carbon atoms are combined with the carbon atoms to which they attached, form a 5- to 7-membered carbocycle or heterocycle comprising: carbon atoms and 0-3 additional heteroatoms selected from N, $NR^{11}$, O, and $S(O)_p$, and 0-2 carbonyl groups, wherein said carbocycle or heterocycle is substituted with 0-4 $R^b$;

$R^6$ is $-(CH_2)_n$-phenyl substituted with 0-3 $R^{6a}$ or $-(CH_2)_n$-pyridyl substituted with 0-3 $R^{6a}$;

$R^{6a}$ is, independently at each occurrence, F, Cl, Br, I, $-(CR^fR^f)_r-OR^c$, $SR^c$, CN, $CF_3$, $OCF_3$, $-(CR^fR^f)_r-NR^{12}R^{13}$, $-C(O)R^c$, $-(CR^fR^f)_r-C(O)OR^c$, $-(CR^fR^f)_r-C(O)NR^{12}R^{13}$, $-Si(Me)_3$, $C_{1-4}$ haloalkyl, $C_{1-4}$ haloalkyloxy-, $C_{1-4}$ alkyloxy-, $C_{1-4}$ alkylthio-, $C_1$-$C_4$ alkyl-C(O)—, $C_{1-4}$ alkyl-O—C(O)—, $C_{1-4}$ alkyl-C(O)NH—, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, $-(CR^fR^f)_r-C_{3-10}$ carbocycle substituted with 0-2 $R^e$, or $-(CR^fR^f)_r$-5- to 10-membered heterocycle comprising: carbon atoms and 1-4 heteroatoms selected from N, $NR^{11}$, O, and $S(O)_p$, wherein said heterocycle is substituted with 0-2 $R^e$;

alternatively, when two $R^{6a}$ groups are attached to adjacent atoms, together with the atoms to which they are attached they form a 5- to 7-membered carbocyclic or heterocyclic ring comprising: carbon atoms and 0-2 heteroatoms selected from N, $NR^{11}$, O, and $S(O)_p$, 0-1 carbonyl and 0-3 ring double bonds, wherein said carbocyclic or heterocyclic ring is substituted with 0-2 $R^b$;

$R^7$ is, independently at each occurrence, F, Cl, Br, I, $OCF_3$, $CF_3$, $OR^c$, $SR^c$, CN, $NO_2$, $-NR^{12}R^{13}$, $-C(O)R^c$, $-C(O)OR^c$, $-C(O)NR^{12}R^{13}$, $-NR^{14}C(O)R^d$, $-S(O)_pNR^{12}R^{13}$, $-S(O)R^d$, $-S(O)_2R^d$, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, $-(CH_2)_r-C_{3-7}$ cycloalkyl substituted with 0-3 $R^b$, $-(CH_2)_r-C_{3-7}$ phenyl substituted with 0-3 $R^b$, or $-(CH_2)_r$-5- to 10-membered heterocycle comprising: carbon atoms and 1-4 heteroatoms selected from N, $NR^{7b}$, O, and $S(O)_p$, wherein said heterocycle is substituted with 0-3 $R^b$;

alternatively, two $R^7$s on two adjacent carbon atoms form a 5- to 7-membered carbocyclic or heterocyclic ring comprising: carbon atoms and 0-3 ring heteroatoms selected from O, N, $NR^{7b}$, and $S(O)_p$;

$R^{7b}$ is H, $C_{1-4}$ alkyl, $-C(O)(C_{1-4}$ alkyl), $-C(O)$phenyl, $-C(O)$benzyl, or benzyl;

$R^{11}$ is, independently at each occurrence, H, $C_{1-6}$ alkyl substituted with 1-5 fluorine, $-(CR^fR^f)_rC(O)NR^{12}R^{13}$, $C_{1-8}$ alkyl substituted with 0-2 $R^a$, $-C(O)(CH_2)_n(C_{3-6}$ cycloalkyl), $-C(O)(CH_2)_n$phenyl, $-C(O)O(C_{1-8}$ alkyl), $-C(O)O(CH_2)_n(C_{3-6}$ cycloalkyl), $-C(O)O(CH_2)_n$phenyl, $-C(O)O(CH_2)_{2-4}(C_{1-4}$ alkyl), $-C(O)NH(C_{1-6}$ alkyl), $-S(O)_2(C_{1-6}$ alkyl), $-S(O)_2(CH_2)_n$phenyl, $-(CR^fR^f)_r-C_{3-7}$ cycloalkyl, $-(CR^fR^f)_r$-phenyl, or $-(CR^fR^f)_r$-5- to 6-membered heterocycle; wherein said alkyl, cycloalkyl, phenyl, and aryl are substituted with 0-2 $R^b$, and said heteroaryl and heterocycle are substituted with 0-2 $R^b$ and comprise: carbon atoms and 1-4 heteroatoms selected from N, $NR^f$, O, and $S(O)_p$;

$R^{12}$ is, independently at each occurrence, H, $C_{1-6}$ alkyl substituted with 1-5 fluorine, $-(CR^fR^f)_rC(O)NR^{12}R^{13}$, $C_{1-6}$ alkyl, $-C(O)(C_{1-6}$ alkyl), $-C(O)(CH_2)_n(C_{6-10}$ aryl), $-C(O)(CH_2)_n$(5- to 10-membered heteroaryl), $-C(O)O(C_{1-4}$ alkyl), $-(CH_2)_nC(O)NH(C_{1-6}$ alkyl), $-(CH_2)_nC(O)NH(C_{6-10}$ aryl), $-(CH_2)_nC(O)NH$(5- to 10-membered heteroaryl), $-S(O)_2(C_{1-6}$ alkyl), $-S(O)_2(CH_2)_n(C_{6-10}$ aryl), $-S(O)_2(CH_2)_n$(5- to 10-membered heteroaryl), $-(CH_2)_n-(C_{6-10}$ aryl), or $-(CH_2)_n$-5- to 10-membered heteroaryl; wherein said alkyl, and aryl are substituted with 0-2 $R^g$; and said heteroaryl is substituted with 0-2 $R^g$ and comprises: carbon atoms and 1-4 heteroatoms selected from N, $NR^{11}$, O, and $S(O)_p$;

R¹³ is, independently at each occurrence, H, $C_{1-6}$ alkyl, or —$(CH_2)_n$-phenyl;

alternatively, $R^{12}$ and $R^{13}$, when attached to the same nitrogen, combine to form a 5- to 10-membered heterocyclic ring comprising: carbon atoms and 1-2 additional heteroatoms selected from N, $NR^{11}$, O, and $S(O)_p$;

$R^{14}$ is, independently at each occurrence, H, $C_{1-6}$ alkyl, or —$(CH_2)_r$-phenyl;

$R^a$ is, independently at each occurrence, F, $OCF_3$, $CF_3$, $OR^c$, $SR^c$, CN, —$NR^{12}R^{13}$, —$C(O)R^c$, —$C(O)OR^c$, —$C(O)NR^{12}R^{13}$, —$NR^{14}C(O)R^d$, —$S(O)_pNR^{12}R^{13}$, —$S(O)R^d$, —$S(O)_2R^d$, —$(CH_2)_r$—$C_{3-10}$ carbocycle substituted with 0-3 $R^e$, or —$(CH_2)_r$-5- to 10-membered heterocycle comprising: carbon atoms and 1-4 heteroatoms selected from N, $NR^f$, O, and $S(O)_p$, wherein said heterocycle is substituted with 0-3 $R^e$;

$R^b$ is, independently at each occurrence, H, =O, F, Cl, Br, I, —$(CH_2)_r$—$OR^c$, $SR^c$, CN, $NO_2$, $CF_3$, $OCF_3$, —$(CH_2)_r$—$NR^{12}R^{13}$, —$C(O)R^c$, —$(CH_2)_rC(O)OR^c$, —$(CH_2)_r$—$C(O)NR^{12}R^{13}$, —$NR^{14}C(O)R^d$, —$S(O)_pNR^{12}R^{13}$, —$S(O)R^d$, —$S(O)_2R^d$, $C_{1-4}$ haloalkyl, $C_{1-4}$ haloalkyloxy-, $C_{1-4}$ alkyloxy-, $C_{1-4}$ alkylthio-, $C_{1-4}$ alkyl-C(O)—, $C_{1-4}$ alkyl-O—C(O)—, $C_{1-4}$ alkyl-C(O)NH—, $C_{1-8}$ alkyl substituted with 0-2 $R^a$, $C_{2-8}$ alkenyl substituted with 0-2-$R^a$, $C_{2-8}$ alkynyl substituted with 0-2 $R^a$, —$(CH_2)_r$—$C_{3-10}$ carbocycle substituted with 0-3 $R^e$, or —$(CH_2)_r$-5- to 10-membered heterocycle comprising: carbon atoms and 1-4 heteroatoms selected from N, $NR^f$, O, and $S(O)_p$, wherein said heterocycle is substituted with 0-3 $R^e$;

$R^c$ is, independently at each occurrence, H, —OP(O)(OEt)$_2$, $C_{1-8}$ alkyl substituted with 0-3 $R^e$, $C_{2-8}$ alkenyl substituted with 0-3 $R^e$, $C_{2-8}$ alkynyl substituted with 0-3 $R^e$, —$(CR^fR^f)_r$—$C_{3-8}$ cycloalkyl substituted with 0-3 $R^e$, —$(CR^fR^f)_r$—$C_{6-10}$ aryl substituted with 0-3 $R^e$, or —$(CR^fR^f)_r$-5- to 10-membered heterocycle comprising: carbon atoms and 1-4 heteroatoms selected from N, $NR^f$, O, and $S(O)_p$, wherein said heterocycle is substituted with 0-3 $R^e$;

$R^d$ is, independently at each occurrence, $CF_3$, OH, $C_{1-4}$ alkoxy, $C_{1-6}$ alkyl, —$(CH_2)_r$—$C_{3-10}$ carbocycle substituted with 0-3 $R^e$, or —$(CH_2)_r$-5- to 10-membered heterocycle comprising: carbon atoms and 1-4 heteroatoms selected from N, $NR^f$, O, and $S(O)_p$, wherein said heterocycle is substituted with 0-3 $R^e$;

$R^e$ is, independently at each occurrence, H, =O, —$(CH_2)_r$—$OR^f$, F, Cl, Br, I, CN, $NO_2$, —$(CH_2)_r$—$NR^{12}R^{13}$, —$C(O)R^f$, —$(CH_2)_r$—$C(O)OR^f$, —$NR^{14}C(O)R^f$, —$(CH_2)_r$—$C(O)NR^{12}R^{13}$, —$SO_2NR^{12}R^{13}$, —$NR^{14}SO_2NR^{12}R^{13}$, —$NR^{14}SO_2$—$C_{1-4}$ alkyl, —$NR^{14}SO_2CF_3$, —$NR^{14}SO_2$-phenyl, —$S(O)_2CF_3$, —$S(O)_p$—$C_{1-4}$ alkyl, —$S(O)_p$-phenyl, —$(CF_2)_rCF_3$, $C_{1-8}$ alkyl substituted with 0-2 $R^g$, $C_{2-8}$ alkenyl substituted with 0-2 $R^g$, $C_{2-8}$ alkynyl substituted with 0-2 $R^g$, —$(CH_2)_r$—$C_{3-8}$ cycloalkyl substituted with 0-2 $R^g$, —$(CH_2)_r$—$C_{6-10}$ aryl substituted with 0-2 $R^g$, or —$(CH_2)_r$-5- to 10-membered heterocycle comprising: carbon atoms and 1-4 heteroatoms selected from N, $NR^f$, O, and $S(O)_p$, wherein said heterocycle is substituted with 0-2 $R^g$;

alternatively, two $R^e$ groups, together with the atoms to which they are attached, form a 5- to 7-membered carbocyclic or heterocyclic ring comprising: carbon atoms and 0-2 heteroatoms selected from N, $NR^f$, O, and $S(O)_p$, 0-1 carbonyl and 0-3 double bonds, wherein said carbocyclic or heterocyclic ring is substituted with 0-3 $R^g$;

$R^f$ is, independently at each occurrence, H, F, $C_{1-6}$ alkyl, or —$(CH_2)_n$-phenyl;

$R^g$ is, independently at each occurrence, H, =O—$OR^f$, F, Cl, Br, I, CN, $NO_2$, —$NR^fR^f$, —$C(O)R^f$, —$C(O)OR^f$, —$NR^fC(O)R^f$, —$C(O)NR^fR^f$, —$SO_2NR^fR^f$, —$NR^fSO_2NR^fR^f$, —$NR^fSO_2$—$C_{1-4}$ alkyl, —$NR^fSO_2CF_3$, —$NR^fSO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl, $C_{2-6}$ alkenyl, or $C_{2-6}$ alkynyl;

n, at each occurrence, is selected from 0, 1, 2, 3, and 4;
p, at each occurrence, is selected from 0, 1, and 2; and
r, at each occurrence, is selected from 0, 1, 2, 3, and 4;

provided that when W is O, A is 2,4-diamino-phenyl, then $R^6$ is other than 2,4-diamino-phenyl.

In a second embodiment, the present invention provides a compound of Formula (I), within the scope of the first embodiment wherein:

ring B is

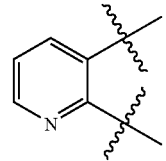

substituted with 0-3 $R^7$;

$R^1$ is, independently at each occurrence, Me, Pr, i-Pr, Bu, t-Bu, F, Cl, Br, OMe, $CF_3$, $OCF_3$, CN, $NO_2$, —$(CH_2)_r$—$OR^c$, —$(CH_2)_r$—$NR^{12}R^{13}$, —$(CH_2)_r$—$CO_2R^c$, —$(CH_2)_r$—$C(O)NR^{12}R^{13}$, $C_{1-4}$ alkyl substituted with 0-2 $R^a$, $C_{2-4}$ alkenyl substituted with 0-2 $R^a$, $C_{2-4}$ alkynyl substituted with 0-2 $R^a$, —$(CH_2)_r$-phenyl substituted with 0-3 $R^b$, or —$(CH_2)_r$-5- to 10-membered heterocycle comprising: carbon atoms and 1-4 heteroatoms selected from N, $NR^{11}$, O, and $S(O)_p$, wherein said heterocycle is substituted with 0-3 $R^b$;

alternatively, two $R^1$s on two adjacent carbon atoms are combined with the carbon atoms to which they attached, form a 5- to 7-membered carbocycle or heterocycle comprising: carbon atoms and 0-2 additional heteroatoms selected from N, NH, O, and $S(O)_p$.

In a third embodiment, the present invention provides a compound of Formula (I), within the scope of the second embodiment wherein: ring A is Ph, 3-$CO_2$Me-Ph, 4-$CO_2$Me-Ph, 4-OBn-Ph, 1,2-dihydroinden-6-yl, 1-naphthyl, or 2-naphthyl.

In a fourth embodiment, the present invention provides a compound of Formula (I), within the scope of the third embodiment wherein: $R^6$ is 2-t-Bu-Ph, or 3-t-Bu-Ph.

In a fifth embodiment, the present invention provides a compound of Formula (I), within the scope of the first embodiment wherein: ring A is Ph, 3-$CO_2$Me-Ph, 4-$CO_2$Me-Ph, 4-OBn-Ph, 1,2-dihydroinden-6-yl, 1-naphthyl, or 2-naphthyl;

ring B is

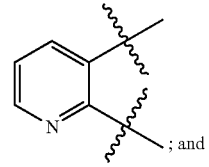

; and $R^6$ is 2-t-Bu-Ph, or 3-t-Bu-Ph.

In a sixth embodiment, the present invention provides a compound selected from the exemplified examples of the present invention or a stereoisomer or pharmaceutically acceptable salt, solvate, or prodrug thereof.

In another embodiment, the present invention provides a compound of Formula (D, wherein: $R^6$ is 2-t-Bu-Ph.

In another embodiment, the present invention provides a compound of Formula (I), wherein: W is O.

In a seventh embodiment, the present invention provides, inter alia, a method for treating a thromboembolic disorder, comprising: administering to a patient in need thereof a therapeutically effective amount of a compound of Formula (I):

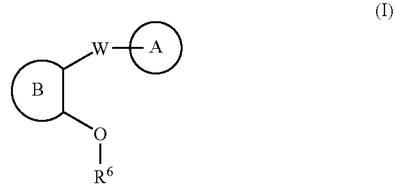

(I)

or a stereoisomer, tautomer, pharmaceutically acceptable salt, solvate, or prodrug thereof, wherein:

A is a $C_{3-13}$ carbocycle substituted with 0-4 $R^1$;

ring B is phenylene substituted with 0-3 $R^7$ or a 5- to 6-membered heteroaryl comprising: carbon atoms and 1-4 ring heteroatoms selected from N, $NR^{11}$, N→O, $S(O)_p$, and 0, wherein said heteroaryl is substituted with 0-4 $R^7$; provided that ring B is other than phenylene substituted with —C(O)$OR^c$;

W is NH, O, or S;

$R^1$ is, independently at each occurrence, =O, F, Cl, Br, I, $CF_3$, —$CF_2CF_3$, $OCF_3$, —$OCF_2CF_2H$, —$OCF_2CF_3$, $SiMe_3$, —$(CR^fR^f)_r$—$OR^c$, $SR^c$, CN, $NO_2$, —$(CR^fR^f)_r$—$NR^{12}R^{13}$, —$(CR^fR^f)_r$—C(O)$R^c$, —$(CR^fR^f)_r$—$CO_2R^c$, —$(CR^fR^f)_r$—C(O)$NR^{12}R^{13}$, —OP(O)(OEt)$_2$, 4,4,5,5-tetramethyl-1,3,2-dioxaborolanyl, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —$(CR^fR^f)_r$—$C_{3-13}$ carbocycle substituted with 0-5 $R^b$, or —$(CR^fR^f)_r$-5- to 10-membered heterocycle comprising: carbon atoms and 1-4 heteroatoms selected from N, $NR^{11}$, O, and $S(O)_p$, wherein said heterocycle is substituted with 0-5 $R^b$;

alternatively, two $R^1$s on two adjacent carbon atoms are combined with the carbon atoms to which they attached, form a 5- to 7-membered carbocycle or heterocycle comprising: carbon atoms and 0-3 additional heteroatoms selected from N, $NR^{11}$, O, and $S(O)_p$, and 0-2 carbonyl groups, wherein said carbocycle or heterocycle is substituted with 0-4 $R^b$;

$R^6$ is —$(CH_2)_n$-phenyl substituted with 0-3 $R^{6a}$ or —$(CH_2)_n$-pyridyl substituted with 0-3 $R^{6a}$;

$R^{6a}$ is, independently at each occurrence, F, Cl, Br, I, —$(CR^fR^f)_r$—$OR^c$, $SR^c$, CN, $CF_3$, $OCF_3$, —$(CR^fR^f)_r$—$NR^{12}R^{13}$, —C(O)$R^c$, —$(CR^fR^f)_r$—C(O)$OR^c$, —$(CR^fR^f)_r$—C(O)$NR^{12}R^{13}$, —Si(Me)$_3$, $C_{1-4}$ haloalkyl, $C_{1-4}$ haloalkyloxy-, $C_{1-4}$ alkyloxy-, $C_{1-4}$ alkylthio-, $C_1$-$C_4$ alkyl-C(O)—, $C_{1-4}$ alkyl-O—C(O)—, $C_{1-4}$ alkyl-C(O)NH—, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —$(CR^fR^f)_r$—$C_{3-10}$ carbocycle substituted with 0-2 $R^e$, or —$(CR^fR^f)_r$-5- to 10-membered heterocycle comprising: carbon atoms and 1-4 heteroatoms selected from N, $NR^{11}$, O, and $S(O)_p$, wherein said heterocycle is substituted with 0-2 $R^e$;

alternatively, when two $R^{6a}$ groups are attached to adjacent atoms, together with the atoms to which they are attached they form a 5- to 7-membered carbocyclic or heterocyclic ring comprising: carbon atoms and 0-2 heteroatoms selected from N, $NR^{11}$, O, and $S(O)_p$, 0-1 carbonyl and 0-3 ring double bonds, wherein said carbocyclic or heterocyclic ring is substituted with 0-2 $R^b$;

$R^7$ is, independently at each occurrence, F, Cl, Br, I, $OCF_3$, $CF_3$, $OR^c$, $SR^c$, CN, $NO_2$, —$NR^{12}R^{13}$, —C(O)$R^c$, —C(O)$OR^c$, —C(O)$NR^{12}R^{13}$, —$NR^{14}C(O)R^d$, —$S(O)_pNR^{12}R^{13}$, —$S(O)R^d$, —$S(O)_2R^d$, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —$(CH_2)_r$—$C_{3-7}$ cycloalkyl substituted with 0-3 $R^b$, —$(CH_2)_r$—$C_{3-7}$ phenyl substituted with 0-3 $R^b$, or —$(CH_2)_r$-5- to 10-membered heterocycle comprising: carbon atoms and 1-4 heteroatoms selected from N, $NR^{7b}$, O, and $S(O)_p$, wherein said heterocycle is substituted with 0-3 $R^b$;

alternatively, two $R^7$s on two adjacent carbon atoms form a 5- to 7-membered carbocyclic or heterocyclic ring comprising: carbon atoms and 0-3 ring heteroatoms selected from O, N, $NR^{7b}$, and $S(O)_p$;

$R^{7b}$ is H, $C_{1-4}$ alkyl, —C(O)($C_{1-4}$ alkyl), —C(O)phenyl, —C(O)benzyl, or benzyl;

$R^{11}$ is, independently at each occurrence, H, $C_{1-6}$ alkyl substituted with 1-5 fluorine, —$(CR^fR^f)_r$C(O)$NR^{12}R^{13}$, $C_{1-8}$ alkyl substituted with 0-2 $R^a$, —C(O)$(CH_2)_n$($C_{3-6}$ cycloalkyl), —C(O)$(CH_2)_n$phenyl, —C(O)O($C_{1-8}$ alkyl), —C(O)O$(CH_2)_n$($C_{3-6}$ cycloalkyl), —C(O)O$(CH_2)_n$phenyl, —C(O)O$(CH_2)_{2-4}$($C_{1-4}$ alkyl), —C(O)NH($C_{1-6}$ alkyl), —$S(O)_2$($C_{1-6}$ alkyl), —$S(O)_2(CH_2)_n$phenyl, —$(CR^fR^f)_r$$C_{3-7}$ cycloalkyl, —$(CR^fR^f)_r$-phenyl, or —$(CR^fR^f)_r$-5- to 6-membered heterocycle; wherein said alkyl, cycloalkyl, phenyl, and aryl are substituted with 0-2 $R^b$, and said heteroaryl and heterocycle are substituted with 0-2 $R^b$ and comprise: carbon atoms and 1-4 heteroatoms selected from N, $NR^f$, O, and $S(O)_p$;

$R^{12}$ is, independently at each occurrence, H, $C_{1-6}$ alkyl substituted with 1-5 fluorine, —$(CR^fR^f)_r$C(O)$NR^{12}R^{13}$, $C_{1-6}$ alkyl, —C(O)($C_{1-6}$ alkyl), —C(O)$(CH_2)_n$($C_{6-10}$ aryl), —C(O)$(CH_2)_n$(5- to 10-membered heteroaryl), —C(O)O ($C_{1-4}$ alkyl), —$(CH_2)_n$C(O)NH($C_{1-6}$ alkyl), —$(CH_2)_n$C(O) NH($C_{6-10}$ aryl), —$(CH_2)_n$C(O)NH(5- to 10-membered heteroaryl), —$S(O)_2$($C_{1-6}$ alkyl), —$S(O)_2(CH_2)_n$($C_{6-10}$ aryl), —$S(O)_2(CH_2)_n$(5- to 10-membered heteroaryl), —$(CH_2)_n$—($C_{6-10}$ aryl), or —$(CH_2)_n$-5- to 10-membered heteroaryl; wherein said alkyl, and aryl are substituted with 0-2 $R^g$; and said heteroaryl is substituted with 0-2 $R^g$ and comprises: carbon atoms and 1-4 heteroatoms selected from N, $NR^{11}$, O, and $S(O)_p$;

$R^{13}$ is, independently at each occurrence, H, $C_{1-6}$ alkyl, or —$(CH_2)_n$-phenyl;

alternatively, $R^{12}$ and $R^{13}$, when attached to the same nitrogen, combine to form a 5- to 10-membered heterocyclic ring comprising: carbon atoms and 1-2 additional heteroatoms selected from N, $NR^{11}$, O, and $S(O)_p$;

$R^{14}$ is, independently at each occurrence, H, $C_{1-6}$ alkyl, or —$(CH_2)_r$-phenyl;

$R^a$ is, independently at each occurrence, F, $OCF_3$, $CF_3$, $OR^c$, $SR^c$, CN, —$NR^{12}R^{13}$, —C(O)$R^c$, —C(O)$OR^c$, —C(O) $NR^{12}R^{13}$, —$NR^{14}C(O)R^d$, —$S(O)_pNR^{12}R^{13}$, —$S(O)R^d$, —$S(O)_2R^d$, —$(CH_2)_r$—$C_{3-10}$ carbocycle substituted with 0-3 $R^e$, or —$(CH_2)_r$-5- to 10-membered heterocycle comprising: carbon atoms and 1-4 heteroatoms selected from N, $NR^f$, O, and $S(O)_p$, wherein said heterocycle is substituted with 0-3 $R^e$;

$R^b$ is, independently at each occurrence, H, =O, F, Cl, Br, I, —$(CH_2)_r$—$OR^c$, $SR^c$, CN, $NO_2$, $CF_3$, $OCF_3$, —$(CH_2)_r$—$NR^{12}R^{13}$, —C(O)$R^c$, —$(CH_2)_rC(O)OR^c$, —$(CH_2)_r$—C(O) $NR^{12}R^{13}$, —$NR^{14}C(O)R^d$, —$S(O)_pNR^{12}R^{13}$, —$S(O)R^d$, —$S(O)_2R^d$, $C_{1-4}$ haloalkyl, $C_{1-4}$ haloalkyloxy-, $C_4$ alkyloxy-, $C_{1-4}$ alkylthio-, $C_{1-4}$ alkyl-C(O)—, $C_{1-4}$ alkyl-O—C(O)—, $C_{1-4}$ alkyl-C(O)NH—, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —(CH$_2$)$_r$—C$_{3-10}$ carbocycle substituted with 0-3 $R^e$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-3 $R^e$;

$R^c$ is, independently at each occurrence, H, —OP(O)(OEt)$_2$, $C_{1-8}$ alkyl substituted with 0-3 $R^e$, $C_{2-8}$ alkenyl substituted with 0-3 $R^e$, $C_{2-8}$ alkynyl substituted with 0-3 $R^e$, —(CR$^f$R$^f$)$_r$—C$_{3-8}$ cycloalkyl substituted with 0-3 $R^e$, —(CR$^f$R$^f$)$_r$—C$_{6-10}$ aryl substituted with 0-3 $R^e$, or —(CR$^f$R$^f$)$_r$-5- to 10-membered heterocycle comprising: carbon atoms and 1-4 heteroatoms selected from N, NR$^f$, O, and S(O)$_p$, wherein said heterocycle is substituted with 0-3 $R^e$;

$R^d$ is, independently at each occurrence, CF$_3$, OH, $C_{1-4}$ alkoxy, $C_{1-6}$ alkyl, —(CH$_2$)$_r$—C$_{3-10}$ carbocycle substituted with 0-3 $R^e$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-3 $R^e$;

$R^e$ is, independently at each occurrence, H, =O, —(CH$_2$)$_r$—OR$^f$, F, Cl, Br, I, CN, NO$_2$, —(CH$_2$)$_r$—NR$^{12}$R$^{13}$, —C(O)R$^f$, —(CH$_2$)$_r$—C(O)OR$^f$, —NR$^{14}$C(O)R$^f$, —(CH$_2$)$_r$—C(O)NR$^{12}$R$^{13}$, —SO$_2$NR$^{12}$R$^{13}$, —NR$^{14}$SO$_2$NR$^{12}$R$^{13}$, —NR$^{14}$SO$_2$—C$_{1-4}$ alkyl, —NR$^{14}$SO$_2$CF$_3$, —NR$^{14}$SO$_2$-phenyl, —S(O)$_2$CF$_3$, —S(O)$_p$—C$_{1-4}$ alkyl, —S(O)$_p$-phenyl, —(CF$_2$)$_r$CF$_3$, $C_{1-8}$ alkyl substituted with 0-2 $R^g$, $C_{2-8}$ alkenyl substituted with 0-2 $R^g$, $C_{2-8}$ alkynyl substituted with 0-2 $R^g$, —(CH$_2$)$_r$—C$_{3-8}$ cycloalkyl substituted with 0-2 $R^g$, —(CH$_2$)$_r$—C$_{6-10}$ aryl substituted with 0-2 $R^g$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-2 $R^g$;

alternatively, two $R^e$ groups, together with the atoms to which they are attached, form a 5- to 7-membered carbocyclic or heterocyclic ring comprising: carbon atoms and 0-2 heteroatoms selected from N, NR$^f$, O, and S(O)$_p$, 0-1 carbonyl and 0-3 double bonds, wherein said carbocyclic or heterocyclic ring is substituted with 0-3 $R^g$;

$R^f$ is, independently at each occurrence, H, F, $C_{1-6}$ alkyl, or —(CH$_2$)$_n$-phenyl;

$R^g$ is, independently at each occurrence, H, =O, OR$^f$, F, Cl, Br, I, CN, NO$_2$, —NR$^f$R$^f$, —C(O)R$^f$, —C(O)OR$^f$, —NR$^f$C(O)R$^f$, —C(O)NR$^f$R$^f$, —SO$_2$NR$^f$R$^f$, —NR$^f$SO$_2$NR$^f$R$^f$, —NR$^f$SO$_2$—C$_{1-4}$ alkyl, —NR$^f$SO$_2$CF$_3$, —NR$^f$SO$_2$-phenyl, —S(O)$_2$CF$_3$, —S(O)$_p$—C$_{1-4}$ alkyl, —S(O)$_p$-phenyl, —(CF$_2$)$_r$CF$_3$, $C_{1-6}$ alkyl, $C_{2-6}$ alkenyl, or $C_{2-6}$ alkynyl;

n, at each occurrence, is selected from 0, 1, 2, 3, and 4;

p, at each occurrence, is selected from 0, 1, and 2; and r, at each occurrence, is selected from 0, 1, 2, 3, and 4.

In an eighth embodiment, the present invention provides a method for treating a thromboembolic disorder, comprising: administering to a patient in need thereof a therapeutically effective amount of a compound of Formula (I), within the scope of the seventh embodiment wherein:

ring A is a carbocycle substituted with 0-3 $R^1$ and selected from cyclohexyl, phenyl, indenyl, dihydroindenyl, naphthyl, dihydronaphthyl, and tetrahydronaphthyl;

ring B is phenylene substituted with 0-3 $R^7$ or pyridylene substituted with 0-3 $R^7$; provided that ring B is other than phenylene substituted with —C(O)OR$^c$;

W is NH or O; and $R^6$ is phenyl substituted with 0-3 $R^{6a}$.

In a ninth embodiment, the present invention provides a method for treating a thromboembolic disorder, comprising: administering to a patient in need thereof a therapeutically effective amount of a compound of Formula (I), within the scope of the eighth embodiment wherein: ring B is pyridylene substituted with 0-3 $R^7$.

In another embodiment, the present invention provides, inter alia, a method for treating a thromboembolic disorder, comprising: administering to a patient in need thereof a therapeutically effective amount of a compound of Formula (Ia):

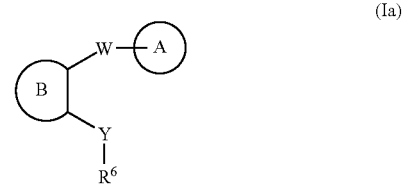

(Ia)

or a stereoisomer, tautomer, pharmaceutically acceptable salt, solvate, or prodrug thereof, wherein:

A is a $C_{3-13}$ carbocycle substituted with 0-5 $R^1$;

ring B is phenylene substituted with 0-4 $R^7$ or a 5- to 6-membered heteroaryl comprising: carbon atoms and 1-4 ring heteroatoms selected from N, NR$^{11}$, N→O, S(O)$_p$, and O, wherein said heteroaryl is substituted with 0-4 $R^7$; provided that ring B is other than phenylene substituted with —C(O)OR$^c$;

W is NH, O, or S;

Y is O, S, NH, —OCR$^{18}$R$^{19}$—, —CH=CH—, or —CONH—;

$R^1$ is, independently at each occurrence, =O, F, Cl, Br, I, CF$_3$, —CF$_2$CF$_3$, OCF$_3$, —OCF$_2$CF$_2$H, —OCF$_2$CF$_3$, SiMe$_3$, —(CR$^f$R$^f$)$_r$—OR$^c$, SR$^c$, CN, NO$_2$, —(CR$^f$R$^f$)$_r$—NR$^{12}$R$^{13}$, —(CR$^f$R$^f$)$_r$—C(O)R$^c$, —(CR$^f$R$^f$)$_r$—CO$_2$R$^c$, —(CR$^f$R$^f$)$_r$—C(O)NR$^{12}$R$^{13}$, —C(O)NR$^{14}$(CR$^f$R$^f$)$_n$N$^{12}$R$^{13}$, —(CR$^f$R$^f$)$_r$OC(O)NR$^{12}$R$^{13}$, —(CR$^f$R$^f$)$_r$—NR$^{14}$C(O)NR$^{12}$R$^{13}$, —(CR$^f$R$^f$)$_r$—NR$^{14}$C(O)R$^d$, —(CR$^f$R$^f$)$_r$—NR$^{14}$C(O)OR$^h$, —NR$^{14}$(CR$^f$R$^f$)$_n$C(O)R$^d$, —NR$^{14}$CO(CR$^f$R$^f$)$_n$OR$^c$, —(CH$_2$)$_r$—CR$^{13}$(=NOR$^c$), —S(O)$_p$NR$^{12}$R$^{13}$, —(CR$^f$R$^f$)$_r$—NR$^{14}$S(O)$_p$NR$^{12}$R$^{13}$, —NR$^{14}$SO$_2$CF$_3$, —NR$^{14}$S(O)$_p$R$^d$, —S(O)$_2$CF$_3$, —S(O)R$^d$, —S(O)$_2$R$^d$, —OP(O)(OEt)$_2$, —O(CH$_2$)$_2$OP(O)(OEt)$_2$, —N(C$_{1-4}$ alkyl)$_3$$^+$Cl$^-$, 4,4,5,5-tetramethyl-1,3,2-dioxaborolanyl, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —(CR$^f$R$^f$)$_r$—C$_{3-13}$ carbocycle substituted with 0-5 $R^b$, or —(CR$^f$R$^f$)$_r$-5- to 10-membered heterocycle comprising: carbon atoms and 1-4 heteroatoms selected from N, NR$^{11}$, O, and S(O)$_p$, wherein said heterocycle is substituted with 0-5 $R^b$;

alternatively, two $R^1$s on two adjacent carbon atoms are combined with the carbon atoms to which they attached, form a 5- to 7-membered carbocycle or heterocycle comprising: carbon atoms and 0-3 additional heteroatoms selected from N, NR$^{11}$, O, and S(O)$_p$, and 0-2 carbonyl groups, wherein said carbocycle or heterocycle is substituted with 0-4 $R^b$;

$R^6$ is —(CR$^f$R$^f$)$_n$-phenyl substituted with 0-3 $R^{6a}$ or —(CR$^f$R$^f$)$_n$-pyridyl substituted with 0-3 $R^{6a}$;

$R^{6a}$ is, independently at each occurrence, F, Cl, Br, I, —(CR$^f$R$^f$)$_r$—OR$^c$, SR$^c$, CN, NO$_2$, CF$_3$, OCF$_3$, —CF$_2$CF$_3$, —OCF$_2$CF$_2$H, —OCF$_2$CF$_3$, —(CR$^f$R$^f$)$_r$—NR$^{12}$R$^{13}$, —C(O)R$^c$, —(CR$^f$R$^f$)$_r$—C(O)OR$^c$, —(CR$^f$R$^f$)$_r$—C(O)NR$^{12}$R$^{13}$, —(CR$^f$R$^f$)$_r$—NR$^{14}$C(O)R$^d$, —S(O)$_p$NR$^{12}$R$^{13}$, —S(O)R$^d$, —S(O)$_2$R$^d$, Si(Me)$_3$, Si(C$_{1-4}$ alkyl)$_3$, $C_{1-4}$ haloalkyl, $C_{1-4}$ haloalkyloxy-, $C_{1-4}$ alkyloxy-, $C_{1-4}$ alkylthio-, $C_1$-C$_4$ alkyl-C (O)—, $C_{1-4}$ alkyl-O—C(O)—, $C_{1-4}$ alkyl-C(O)NH—, $C_{1-8}$ alkyl substituted with 0-1 $R^a$, $C_{2-8}$ alkenyl substituted with 0-1 $R^a$, $C_{2-8}$ alkynyl substituted with 0-1 $R^a$, —$(CR^fR^f)_r$—$C_{3-10}$ carbocycle substituted with 0-2 $R^e$, or —$(CR^fR^f)_r$-5- to 10-membered heterocycle comprising: carbon atoms and 1-4 heteroatoms selected from N, $NR^{11}$, O, and $S(O)_p$, wherein said heterocycle is substituted with 0-2 $R^e$;

alternatively, when two $R^{6a}$ groups are attached to adjacent atoms, together with the atoms to which they are attached they form a 5- to 7-membered carbocyclic or heterocyclic ring comprising: carbon atoms and 0-2 heteroatoms selected from N, $NR^{11}$, O, and $S(O)_p$, 0-1 carbonyl and 0-3 ring double bonds, wherein said carbocyclic or heterocyclic ring is substituted with 0-2 $R^b$;

$R^7$ is, independently at each occurrence, F, Cl, Br, I, $OCF_3$, $CF_3$, $OR^c$, $SR^c$, CN, $NO_2$, —$NR^{12}R^{13}$, —$C(O)R^c$, —$C(O)OR^c$, —$C(O)NR^{12}R^{13}$, —$NR^{14}C(O)R^d$, —$S(O)_pNR^{12}R^{13}$, —$S(O)R^d$, —$S(O)_2R^d$, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —$(CR^fR^f)_r$—$C_{3-10}$ carbocycle substituted with 0-3 $R^b$, or —$(CR^fR^f)_r$-5- to 10-membered heterocycle comprising: carbon atoms and 1-4 heteroatoms selected from N, $NR^{7b}$, O, and $S(O)_p$, wherein said heterocycle is substituted with 0-3 $R^b$;

alternatively, two $R^7$s on two adjacent carbon atoms form a 5- to 7-membered carbocyclic or heterocyclic ring comprising: carbon atoms and 0-3 ring heteroatoms selected from O, N, $NR^{7b}$, and $S(O)_p$, wherein said carbocyclic or heterocyclic ring is substituted with 0-2 $R^{7c}$;

$R^{7b}$ is H, $C_{1-4}$ alkyl, —$C(O)(C_{1-4}$ alkyl), —C(O)phenyl, —C(O)benzyl, or benzyl;

$R^{7c}$ is, independently at each occurrence, H, F, Cl, Br, I, $OCF_3$, $CF_3$, $OR^c$, $SR^c$, CN, $NO_2$, —$NR^{12}R^{13}$, —$C(O)R^c$, —$C(O)OR^c$, —$C(O)NR^{12}R^{13}$, —$NR^{14}C(O)R^d$, —$S(O)_pNR^{12}R^{13}$, —$S(O)R^d$, —$S(O)_2R^d$, $C_{1-4}$ alkyl, phenyl substituted with 0-3 $R^b$, or benzyl substituted with 0-3 $R^b$;

$R^{11}$ is, independently at each occurrence, H, $C_{1-6}$ alkyl substituted with 1-5 fluorine, —$(CR^fR^f)_rC(O)NR^{12}R^{13}$, $C_{1-8}$ alkyl substituted with 0-2 $R^a$, $C_{2-4}$ alkenyl substituted with 0-1 $R^a$, $C_{2-4}$ alkynyl substituted with 0-1 $R^a$, —$C(O)(C_{1-6}$ alkyl), —$C(O)(CH_2)_n(C_{3-6}$ cycloalkyl), —$C(O)(CH_2)_n(C_{6-10}$ aryl), —$C(O)(CH_2)_n$(5- to 10-membered heteroaryl), —$C(O)O(C_{1-8}$ alkyl), —$C(O)O(CH_2)_n(C_{3-6}$ cycloalkyl), —$C(O)O(CH_2)_n(C_{6-10}$ aryl), —$C(O)O(CH_2)_n$(5- to 10-membered heteroaryl), —$C(O)O(CH_2)_{2-4}(C_{1-4}$ alkyl), —$C(O)NH(C_{1-8}$ alkyl), —$C(O)NH(CH_2)_n(C_{3-6}$ cycloalkyl), —$C(O)NH(CH_2)_n(C_{6-10}$ aryl), —$C(O)NH(CH_2)_n$(5- to 10-membered heteroaryl), —$S(O)_2(C_{1-8}$ alkyl), —$S(O)_2(CH_2)_n(C_{3-6}$ cycloalkyl), —$S(O)_2(CH_2)_n(C_{6-10}$ aryl), —$S(O)_2(CH_2)_n$(5- to 10-membered heteroaryl), —$(CR^fR^f)_r$—$C_{3-7}$ cycloalkyl, —$(CR^fR^f)_r$-phenyl, or —$(CR^fR^f)_r$-5- to 6-membered heterocycle; wherein said alkyl, cycloalkyl, phenyl, and aryl are substituted with 0-2 $R^b$, and said heteroaryl and heterocycle are substituted with 0-2 $R^b$ and comprise: carbon atoms and 1-4 heteroatoms selected from N, $NR^f$, O, and $S(O)_p$;

$R^{12}$ is, independently at each occurrence, H, $C_{1-6}$ alkyl substituted with 1-5 fluorine, —$(CR^fR^f)_rC(O)NR^{12}R^{13}$, $C_{1-6}$ alkyl, —$C(O)(C_{1-6}$ alkyl), —$C(O)(CH_2)_n(C_{6-10}$ aryl), —$C(O)(CH_2)_n$(5- to 10-membered heteroaryl), —$C(O)O(C_{1-4}$ alkyl), —$C(O)OCH_2(C_{6-10}$ aryl), —$(CH_2)_nC(O)OCH_2$(5- to 10-membered heteroaryl), —$(CH_2)_nOC(O)(C_{1-4}$ alkyl), —$(CH_2)_nOC(O)(C_{6-10}$ aryl), —$(CH_2)_nOC(O)$(5- to 10-membered heteroaryl), —$(CH_2)_nC(O)O(C_{1-4}$ alkyl), —$(CH_2)_nC(O)O(C_{6-10}$ aryl), —$(CH_2)_nC(O)O$(5- to 10-membered heteroaryl), —$(CH_2)_nC(O)NH(C_{1-6}$ alkyl), —$(CH_2)_nC(O)NH(C_{6-10}$ aryl), —$(CH_2)_nC(O)NH$(5- to 10-membered heteroaryl), —$(CH_2)_rOC(O)NH(C_{1-6}$ alkyl), —$(CH_2)_rOC(O)NH(C_{6-10}$ aryl), —$(CH_2)_rOC(O)NH$(5- to 10-membered heteroaryl), —$S(O)_2(C_{1-6}$ alkyl), —$S(O)_2(CH_2)_n(C_{6-10}$ aryl), —$S(O)_2(CH_2)_n$(5- to 10-membered heteroaryl), —$(CH_2)_n$—$(C_{6-10}$ aryl), or —$(CH_2)_n$-5- to 10-membered heteroaryl; wherein said alkyl and aryl are substituted with 0-2 $R^g$; and said heteroaryl is substituted with 0-2 $R^g$ and comprises: carbon atoms and 1-4 heteroatoms selected from N, $NR^{11}$, O, and $S(O)_p$;

$R^{13}$ is, independently at each occurrence, H, $C_{1-6}$ alkyl, or —$(CH_2)_n$-phenyl;

alternatively, $R^{12}$ and $R^{13}$, when attached to the same nitrogen, combine to form a 5- to 10-membered heterocyclic ring comprising: carbon atoms and 1-2 additional heteroatoms selected from N, $NR^{11}$, O, and $S(O)_p$;

$R^{14}$ is, independently at each occurrence, H, $C_{1-6}$ alkyl substituted with 0-2 $R^{14a}$, $C_{2-6}$ alkenyl substituted with 0-2 $R^{14a}$, $C_{2-6}$ alkynyl substituted with 0-2 $R^{14a}$, —$(CH_2)_r$—$C_{3-10}$ carbocycle substituted with 0-3 $R^g$, or —$(CH_2)_r$-5- to 10-membered heterocycle comprising: carbon atoms and 1-4 heteroatoms selected from N, $NR^{11}$, O, and $S(O)_p$, wherein said heterocycle is substituted with 0-3 $R^g$;

$R^{14a}$ is, independently at each occurrence, H, $C_{1-4}$ alkyl, $OR^f$, Cl, F, Br, I, =O, $CF_3$, CN, $NO_2$, $NR^{12}R^{13}$, —$C(O)R^f$, —$C(O)OR^f$, —$C(O)NR^{12}R^{13}$, or —$S(O)_pR^f$;

$R^{18}$ is, independently at each occurrence, H, F, or $C_{1-6}$ alkyl;

$R^{19}$ is, independently at each occurrence, H, OH, —$C(O)OR^f$, or $C_{1-6}$ alkyl;

$R^a$ is, independently at each occurrence, H, =O, F, $OCF_3$, $CF_3$, —$(CR^fR^f)_rOR^c$, —$(CR^fR^f)_rSR^c$, CN, —$(CR^fR^f)_rNR^{12}R^{13}$, —$(CR^fR^f)_rC(O)R^c$, —$(CR^fR^f)_rC(O)OR^c$, —$(CR^fR^f)_rC(O)NR^{12}R^{13}$, —$(CR^fR^f)_rNR^{14}C(O)R^d$, —$(CR^fR^f)_rS(O)_pNR^{12}R^{13}$, —$(CR^fR^f)_rS(O)R^d$, —$(CR^fR^f)_rS(O)_2R^d$, $C_{1-4}$ alkyl substituted with 1-5 fluorine, —$(CH_2)_r$—$C_{3-10}$ carbocycle substituted with 0-3 $R^e$, or —$(CH_2)_r$-5- to 10-membered heterocycle comprising: carbon atoms and 1-4 heteroatoms selected from N, $NR^f$, O, and $S(O)_p$, wherein said heterocycle is substituted with 0-3 $R^e$;

$R^b$ is, independently at each occurrence, —H, =O, F, Cl, Br, I, —$(CH_2)_r$—$OR^c$, $SR^c$, CN, $NO_2$, $CF_3$, $OCF_3$, —$(CR^fR^f)_rNR^{12}R^{13}$, —$C(O)R^c$, —$(CH_2)_r$—$C(O)OR^c$, —$(CH_2)_rC(O)NR^{12}R^{13}$, —$NR^{14}C(O)R^d$, —$S(O)_pNR^{12}R^{13}$, —$S(O)R^d$, —$S(O)_2R^d$, $C_{1-4}$ haloalkyl, $C_{1-4}$ haloalkyloxy-, $C_{1-4}$ alkyloxy-, $C_{1-4}$ alkylthio-, $C_{1-4}$ alkyl-C(O)—, $C_{1-4}$ alkyl-O—C(O)—, $C_{1-4}$ alkyl-C(O)NH—, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —$(CH_2)_r$—$C_{3-10}$ carbocycle substituted with 0-3 $R^e$, or —$(CH_2)_r$-5- to 10-membered heterocycle comprising: carbon atoms and 1-4 heteroatoms selected from N, $NR^f$, O, and $S(O)_p$, wherein said heterocycle is substituted with 0-3 $R^e$;

$R^c$ is, independently at each occurrence, H, —$OP(O)(OEt)_2$, $C_{1-8}$ alkyl substituted with 0-3 $R^e$, $C_{2-8}$ alkenyl substituted with 0-3 $R^e$, $C_{2-8}$ alkynyl substituted with 0-3 $R^e$, —$(CR^fR^f)_r$—$C_{3-8}$ cycloalkyl substituted with 0-3 $R^e$, —$(CR^fR^f)_r$—$C_{6-10}$ aryl substituted with 0-3 $R^e$, or —$(CR^fR^f)_r$-5- to 10-membered heterocycle comprising: carbon atoms and 1-4 heteroatoms selected from N, $NR^f$, O, and $S(O)_p$, wherein said heterocycle is substituted with 0-3 $R^e$;

$R^d$ is, independently at each occurrence, $CF_3$, OH, $C_{1-4}$ alkoxy, $C_{1-6}$ alkyl, —$(CH_2)_r$—$C_{3-10}$ carbocycle substituted with 0-3 $R^e$, or —$(CH_2)_r$-5- to 10-membered heterocycle comprising: carbon atoms and 1-4 heteroatoms selected from N, $NR^f$, O, and $S(O)_p$, wherein said heterocycle is substituted with 0-3 $R^e$;

$R^e$ is, independently at each occurrence, H, =O, —$(CH_2)_r$—$OR^f$, F, Cl, Br, I, CN, $NO_2$, —$(CH_2)_r$—$NR^{12}R^{13}$, —C(O)R$^f$, —(CH$_2$)$_r$—C(O)OR$^f$, —NR$^{14}$C(O)R$^f$, —(CH$_2$)$_r$—C(O)NR$^{12}$R$^{13}$, —SO$_2$NR$^{12}$R$^{13}$, —NR$^{14}$SO$_2$NR$^{12}$R$^{13}$, —NR$^{14}$SO$_2$—C$_{1-4}$ alkyl, —NR$^{14}$SO$_2$CF$_3$, —NR$^{14}$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-4}$ alkyl substituted with 0-2 R$^g$, C$_{2-8}$ alkenyl substituted with 0-2 R$^g$, C$_{2-8}$ alkynyl substituted with 0-2 R$^g$, —(CH$_2$)$_r$—C$_{3-8}$ cycloalkyl substituted with 0-2 R$^g$, —(CH$_2$)$_r$—C$_{6-10}$ aryl substituted with 0-2 R$^g$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-2 R$^g$;

alternatively, two R$^e$ groups, together with the atoms to which they are attached, form a 5- to 7-membered carbocyclic or heterocyclic ring comprising: carbon atoms and 0-2 heteroatoms selected from N, NR$^f$, O, and S(O)$_p$, 0-1 carbonyl and 0-3 double bonds, wherein said carbocyclic or heterocyclic ring is substituted with 0-3 R$^g$;

R$^f$ is, independently at each occurrence, H, F, C$_{1-6}$ alkyl, or —(CH$_2$)$_n$-phenyl;

R$^g$ is, independently at each occurrence, H, =O, OR$^f$, F, Cl, Br, I, CN, NO$_2$, —NR$^f$R$^f$, —C(O)R$^f$, —C(O)OR$^f$, —NR$^f$C(O)R$^f$, —C(O)NR$^f$R$^f$, —SO$_2$NR$^f$R, —NR$^f$SO$_2$NR$^f$R$^f$, —NR$^f$SO$_2$—C$_{1-4}$ alkyl, —NR$^f$SO$_2$CF$_3$, —NR$^f$SO$_2$-phenyl, —S(O)$_2$CF$_3$, —S(O)$_p$—C$_{1-4}$ alkyl, —S(O)$_p$-phenyl —(CF$_2$)$_r$CF$_3$, C$_{1-6}$ alkyl, C$_{2-6}$ alkenyl, or C$_{2-6}$ alkynyl;

R$^h$ is, independently at each occurrence, C$_{1-6}$ alkyl substituted with 0-2 R$^g$, or —(CH$_2$)$_n$-phenyl substituted with 0-2 R$^g$;

n, at each occurrence, is selected from 0, 1, 2, 3, and 4;

p, at each occurrence, is selected from 0, 1, and 2;

r, at each occurrence, is selected from 0, 1, 2, 3, and 4; and t, at each occurrence, is selected from 1, 2, 3, and 4.

In another embodiment, the present invention provides a method for treating a thromboembolic disorder, comprising: administering to a patient in need thereof a therapeutically effective amount of a compound of Formula (Ia), wherein: Y is O, S, or NH.

In another embodiment, the present invention provides a method for treating a thromboembolic disorder, comprising: administering to a patient in need thereof a therapeutically effective amount of a compound of Formula (Ia), wherein: ring A is a carbocycle substituted with 0-3 R$^1$ and selected from cyclohexyl-, phenyl, indenyl, dihydroindenyl, naphthyl, dihydronaphthyl, and tetrahydronaphthyl.

In another embodiment, the present invention provides a method for treating a thromboembolic disorder, comprising: administering to a patient in need thereof a therapeutically effective amount of a compound of Formula (I), wherein: ring B is substituted with 0-3 R$^7$ and selected from:

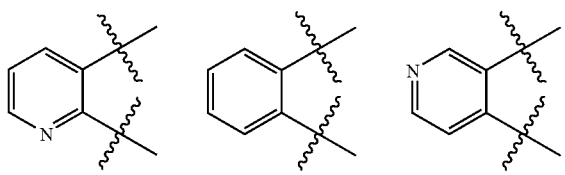

-continued

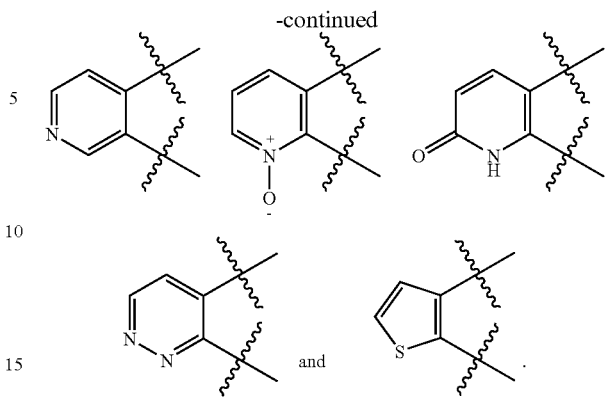

and

In another embodiment, the present invention provides a method for treating a thromboembolic disorder, comprising: administering to a patient in need thereof a therapeutically effective amount of a compound of Formula (Ia), wherein:

R$^1$ is, independently at each occurrence, F, Cl, Br, I, CF$_3$, —CF$_2$CF$_3$, OCF$_3$, —OCF$_2$CF$_2$H, —OCF$_2$CF$_3$, SiMe$_3$, —(CR$^f$R$^f$)$_r$—OR$^c$, SR$^c$, CN, NO$_2$, —(CR$^f$R$^f$)$_r$—NR$^{12}$R$^{13}$, —(CR$^f$R$^f$)$_r$—C(O)R$^c$, —(CR$^f$R$^f$)$_r$—CO$_2$R$^c$, —(CR$^f$R$^f$)$_r$—C(O)NR$^{12}$R$^{13}$, —OP(O)(OEt)$_2$, 4,4,5,5-tetramethyl-1,3,2-dioxaborolanyl, C$_{1-8}$ alkyl substituted with 0-2 R$^a$, C$_{2-8}$ alkenyl substituted with 0-2 R$^a$, C$_{2-8}$ alkynyl substituted with 0-2 R$^a$, —(CR$^f$R$^f$)$_r$—C$_{3-13}$ carbocycle substituted with 0-5 R$^b$, or —(CR$^f$R$^f$)$_r$-5- to 10-membered heterocycle comprising: carbon atoms and 1-4 heteroatoms selected from N, NR$^{11}$, O, and S(O)$_p$, wherein said heterocycle is substituted with 0-5 R$^b$;

alternatively, two R$^1$s on two adjacent carbon atoms are combined with the carbon atoms to which they attached, form a 5- to 7-membered carbocycle or heterocycle comprising: carbon atoms and 0-3 additional heteroatoms selected from N, NR$^{11}$, O, and S(O)$_p$, and 0-2 carbonyl groups, wherein said carbocycle or heterocycle is substituted with 0-4 R$^b$.

In another embodiment, the present invention provides a method for treating a thromboembolic disorder, comprising: administering to a patient in need thereof a therapeutically effective amount of a compound of Formula (Ia), wherein:

R$^6$ is —(CH$_2$)$_n$-phenyl substituted with 0-3 R$^{6a}$ or —(CH$_2$)$_n$-pyridyl substituted with 0-3 R$^{6a}$; and R$^{6a}$ is, independently at each occurrence, F, Cl, Br, I, —(CR$^f$R$^f$)$_r$—OR$^c$, SR$^c$, CN, CF$_3$, OCF$_3$, —CF$_2$CF$_3$, —OCF$_2$CF$_2$H, —OCF$_2$CF$_3$, —NR$^{12}$R$^{13}$, —C(O)R$^c$, —Si(Me)$_3$, C$_{1-4}$ haloalkyl, C$_{1-4}$ haloalkyloxy-, C$_{1-4}$ alkyloxy-, C$_{1-4}$ alkylthio-, C$_1$-C$_4$ alkyl-C(O)—, C$_{1-4}$ alkyl-O—C(O)—, C$_{1-4}$ alkyl-C(O)NH—, C$_{1-8}$ alkyl substituted with 0-2 R$^a$, C$_{2-8}$ alkenyl substituted with 0-2 R$^a$, C$_{2-8}$ alkynyl substituted with 0-2 R$^a$, —(CR$^f$R$^f$)$_r$—C$_{3-10}$ carbocycle substituted with 0-2 R$^e$, or —(CR$^f$R$^f$)$_r$-5- to 10-membered heterocycle comprising: carbon atoms and 1-4 heteroatoms selected from N, NR$^{11}$, O, and S(O)$_p$, wherein said heterocycle is substituted with 0-2 R$^e$;

alternatively, when two R$^{6a}$ groups are attached to adjacent atoms, together with the atoms to which they are attached they form a 5- to 7-membered carbocyclic or heterocyclic ring comprising: carbon atoms and 0-2 heteroatoms selected from N, NR$^{11}$, O, and S(O)$_p$, 0-1 carbonyl and 0-3 ring double bonds, wherein said carbocyclic or heterocyclic ring is substituted with 0-2 R$^b$.

In another embodiment, the present invention provides a method for treating a thromboembolic disorder, comprising:

administering to a patient in need thereof a therapeutically effective amount of a compound of Formula (Ia), wherein: $R^{11}$ is, independently at each occurrence, H, $C_{1-8}$ alkyl substituted with 0-2 $R^a$, —C(O)(CH$_2$)$_n$(C$_{3-6}$ cycloalkyl), —C(O)(CH$_2$)$_n$phenyl, —C(O)O(C$_{1-8}$ alkyl), —C(O)O(CH$_2$)$_n$(C$_{3-6}$ cycloalkyl), —C(O)O(CH$_2$)$_n$phenyl, —C(O)O(CH$_2$)$_{24}$(C$_{1-4}$ alkyl), —C(O)NH(C$_{1-6}$ alkyl), —S(O)$_2$(C$_{1-6}$ alkyl), —S(O)$_2$(CH$_2$)$_n$phenyl, —(CR$^f$R$^f$)$_r$—C$_{3-7}$ cycloalkyl, —(CR$^f$R$^f$)$_r$phenyl, or —(CR$^f$R$^f$)$_r$-5- to 6-membered heterocycle; wherein said alkyl, cycloalkyl, phenyl, and aryl are substituted with 0-2 $R^b$, and said heteroaryl and heterocycle are substituted with 0-2 $R^b$ and comprise: carbon atoms and 1-4 heteroatoms selected from N, NR$^f$, O, and S(O)$_p$.

In another embodiment, the present invention provides a method for treating a thromboembolic disorder, comprising: administering to a patient in need thereof a therapeutically effective amount of a compound of Formula (Ia), wherein: $R^6$ is phenyl substituted with 0-3 $R^{6a}$.

In another embodiment, the present invention provides a method for treating a thromboembolic disorder, comprising: administering to a patient in need thereof a therapeutically effective amount of a compound of Formula (Ia), wherein: W is NH or O.

In another embodiment, the present invention provides a pharmaceutical composition comprising a pharmaceutically acceptable carrier and at least one of the compounds of the present invention or a stereoisomer, tautomer, pharmaceutically acceptable salt, solvate, or prodrug thereof.

In another embodiment, the present invention provides a pharmaceutical composition comprising a pharmaceutically acceptable carrier and a therapeutically effective amount of at least one of the compounds of the present invention or a stereoisomer, tautomer, pharmaceutically acceptable salt, solvate, or prodrug thereof.

In another embodiment, the present invention provides a novel process for making a compound of the present invention or a stereoisomer, tautomer, pharmaceutically acceptable salt, solvate or prodrug thereof.

In another embodiment, the present invention provides a novel intermediate for making a compound of the present invention or a stereoisomer, tautomer, pharmaceutically acceptable salt, solvate or prodrug thereof.

In another embodiment, the present invention provides a pharmaceutical composition further comprising at least one additional therapeutic agent selected from potassium channel openers, potassium channel blockers, calcium channel blockers, sodium hydrogen exchanger inhibitors, antiarrhythmic agents, antiatheroaclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition wherein the additional therapeutic agent(s) is an antihypertensive agent selected from ACE inhibitors, AT-1 receptor antagonists, beta-adrenergic receptor antagonists, ETA receptor antagonists, dual ETA/AT-1 receptor antagonists, and vasopeptidase inhibitors, an antiarrythmic agent selected from IKur inhibitors, an anticoagulants selected from thrombin inhibitors, antithrombin-III activators, heparin co-factor II activators, factor VIIa inhibitors, factor Xa inhibitors, factor XIa inhibitors and kallikrein inhibitors, or antiplatelet agents selected from GPIIb/IIIa blockers, protease activated receptor (PAR-1) antagonists, phosphodiesterase-III inhibitors, other $P2Y_1$ antagonists, $P2Y_{12}$ antagonists, thromboxane receptor antagonists, cyclooxygense-1 inhibitors, and aspirin, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In a preferred embodiment, the present invention provides pharmaceutical composition, wherein the additional therapeutic agent(s) are an anti-platelet agent or a combination thereof.

In a preferred embodiment, the present invention provides a pharmaceutical composition, wherein the additional therapeutic agent is the anti-platelet agent selected from clopidogrel and aspirin, or a combination thereof.

In a preferred embodiment, the present invention provides a pharmaceutical composition, wherein the additional therapeutic agent is the anti-platelet agent clopidogrel.

In another embodiment, the present invention provides a method for modulation of platelet reactivity comprising administering to a patient in need of such treatment a therapeutically effective amount of at least one of the compounds of the present invention or a stereoisomer, tautomer, pharmaceutically acceptable salt, solvate, or prodrug thereof.

In another embodiment, the present invention provides a method for treating thrombotic or thromboembolic disorders comprising: administering to a patient in need of such treatment a therapeutically effective amount of at least one of the compounds of the present invention or a stereoisomer, tautomer, pharmaceutically acceptable salt, solvate, or prodrug thereof.

In another embodiment, the thromboembolic disorder is selected from the group consisting of arterial cardiovascular thromboembolic disorders, venous cardiovascular thromboembolic disorders, arterial cerebrovascular thromboembolic disorders, venous cerebrovascular thromboembolic disorders, and thromboembolic disorders in the chambers of the heart.

In another embodiment, the thromboembolic disorder is selected from the group consisting of unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a method of treating a patient in need of thromboembolic disorder treatment, comprising: administering a compound of the present invention or a stereoisomer, tautomer, pharmaceutically acceptable salt, solvate, or prodrug thereof in an amount effective to treat a thromboembolic disorder.

In another embodiment, the present invention provides a method, comprising: administering a compound of the present invention or a stereoisomer, tautomer, pharmaceutically acceptable salt, solvate, or prodrug thereof in an amount effective to treat a thrombotic or thromboembolic disorder.

In another embodiment, the present invention provides a compound of the present invention for use in therapy.

In another embodiment, the present invention provides a compound of the present invention for use in therapy for treating a thrombotic and thromboembolic disorder.

In another embodiment, the present invention also provides the use of a compound of the present invention for the manufacture of a medicament for the treatment of a thrombotic or thromboembolic disorder.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used for the treatment of a thrombotic or thromboembolic disorder.

In another preferred embodiment, the present invention provides a novel article of manufacture, further comprising: (d) a second container; wherein components (a) and (b) are located within the second container and component (c) is located within or outside of the second container.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used in combination with a second therapeutic agent to treat a thrombotic or thromboembolic disorder.

In another preferred embodiment, the present invention provides a novel article of manufacture, further comprising: (d) a second container; wherein components (a) and (b) are located within the second container and component (c) is located within or outside of the second container.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials or optically active catalysts. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention. The inventive compounds may be in the free or hydrate form.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. When a ring system (e.g., carbocyclic or heterocyclic) is said to be substituted with a carbonyl group or a double bond, it is intended that the carbon atom of the carbonyl group or one carbon atom of the double bond be part of (i.e., within) the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative. In cases wherein there are quaternary carbon atoms on compounds of the present invention, these can be replaced by silicone atoms, provided they do not form Si—N or Si—O bond.

When any variable occurs more than one time in any constituent or formula for a compound, its definition at each occurrence is independent of its definition at every other occurrence. Thus, for example, if a group is shown to be substituted with 0-3 $R^1$, then said group may optionally be substituted with up to three $R^1$ groups and $R^1$ at each occurrence is selected independently from the definition of $R^1$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. For example, "$C_1$-$C_{10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms and one or more unsaturated carbon-carbon bonds which may occur in any stable point along the chain. For example, "$C_2$-$C_6$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration and one or more carbon-carbon triple bonds which may occur in any stable point along the chain. For example, "$C_2$-$C_6$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like.

"Alkoxy" or "alkyloxy" represents an alkyl group as defined above with the indicated number of carbon atoms attached through an oxygen bridge. For example, "$C_1$-$C_6$ alkoxy" (or alkyloxy), is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulphur bridge; for example methyl-S—, ethyl-S—, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$-$C_6$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluoroethoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred carbocycles, unless otherwise specified, are cyclopropyl, cyclobutyl, cyclopentyl, cyclohexyl, phenyl, naphthyl, and indanyl. When the term "carbocycle" is used, it is intended to include "aryl".

As used herein, the term "bicyclic carbocycle" or "bicyclic carbocyclic group" is intended to mean a stable 9- or 10-membered carbocyclic ring system which contains two fused rings and consists of carbon atoms. Of the two fused rings, one ring is a benzo ring fused to a second ring; and the second ring is a 5 or 6 membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

As used herein, the term "aryl", "$C_6$-$C_{10}$ aryl" or "aromatic residue", is intended to mean an aromatic moiety containing, if specified, the specified number of carbon atoms; for example phenyl or naphthyl. Unless otherwise specified, "aryl", "$C_6$-$C_{10}$ aryl" or "aromatic residue" may be unsubstituted or substituted with 0 to 3 groups selected from H, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle" or "heterocyclic group" is intended to mean a stable 3, 4, 5, 6, or 7-membered monocyclic or bicyclic or 7, 8, 9, 10, 11, 12, 13, or 14-membered bicyclic or tricyclic heterocyclic ring which is saturated, partially unsaturated or fully unsaturated, and which consists of carbon atoms and 1, 2, 3 or 4 heteroatoms independently selected from the group consisting of N, O and S; and including any bicyclic group in which any of the above-defined heterocyclic rings is fused to a benzene ring. The nitrogen and sulfur heteroatoms may optionally be oxidized to —NO—, —SO—, or —SO$_2$—. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen atom in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathinyl, phenoxazinyl, phthalazinyl, piperazinyl, piperidinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5 or 6-membered monocyclic aromatic ring comprising a 5 membered heteroaryl ring, a 6-membered heteroaryl ring or a benzo ring, each fused to a second ring. The second ring is a 5 or 6 membered monocyclic ring which is saturated, partially unsaturated, or unsaturated, and comprises a 5 membered heterocycle, a 6 membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinoline, 2,3-dihydro-benzofuranyl, chromanyl, 1,2,3,4-tetrahydro-quinoxaline, and 1,2,3,4-tetrahydro-quinazoline.

Also included are fused ring and spiro compounds containing, for example, the above carbocycles or heterocycles.

Bridged rings are also included in the definition of carbocycle or heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Greene and Wuts, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference. Examples of amine protecting groups include, but are not limited to, the following: (Fmoc); (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, the disclosure of which is hereby incorporated by reference.

Isotopically labeled compounds of the present invention, i.e., wherein one or more of the atoms described are replaced by an isotope of that atom (e.g., C replaced by $^{13}$C or by $^{14}$C; and isotopes of hydrogen include tritium and deuterium), are also provided herein. Such compounds have a variety of potential uses, e.g., as standards and reagents in determining the ability of a potential pharmaceutical to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 99% compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Design of Prodrugs, edited by H. Bundgaard, (Elsevier, 1985), and *Methods in Enzymology,* Vol. 112, at pp. 309-396, edited by K. Widder, et. al. (Academic Press, 1985);

b) A Textbook of Drug Design and Development, edited by Krosgaard-Larsen and H. Bundgaard, Chapter 5, "*Design and Application of Prodrugs,*" by H. Bundgaard, at pp. 113-191 (1991);

c) H. Bundgaard, *Advanced Drug Delivery Reviews,* Vol. 8, p. 1-38 (1992);

d) H. Bundgaard, et al., *Journal of Pharmaceutical Sciences,* Vol. 77, p. 285 (1988); and e) N. Kakeya, et. al., *Chem Phar Bull., Vol.* 32, p. 692 (1984).

Compounds containing a carboxy group can form physiologically hydrolyzable esters which serve as prodrugs by being hydrolyzed in the body to yield compounds of the present invention per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$ alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)-methyl, and other well known physiologically hydrolyzable esters used, for example, in the penicillin and cephalosporin arts. Such esters may be prepared by conventional techniques known in the art.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates and the like. Methods of solvation are generally known in the art.

As used herein, the term "patient" encompasses all mammalian species.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination with other active ingredients to inhibit $P2Y_1$ or to treat the conditions or disorders listed herein. When applied to a combination, the term refers to combined amounts of the active ingredients that result in the therapeutic effect, whether administered in combination, serially or simultaneously. The combination of compounds is preferably a synergistic combination. Synergy, as described, for example, by Chou and Talalay, *Adv. Enzyme Regul.* 1984, 22:27-55, occurs when the effect (in this case, inhibition of $P2Y_1$) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased anti-thrombotic effect, or some other beneficial effect of the combination compared with the individual components.

The term "pharmaceutical composition" means a composition comprising a compound of the invention in combination with at least one additional pharmaceutical carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 18th ed., 1990, which is incorporated herein by reference in its entirety.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "M" for molar, "mmol" for millimole or millimoles, "min" for minute or minutes, "h" for hour or hours, "rt" for room temperature, "attn" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "LC-MS" for liquid chromatography mass spectrometry, "HPLC" for high pressure liquid chromatography, "RP HPLC" for reverse phase HPLC, "TLC" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, "tlc" for thin layer chromatography, and "α", "β", "R", "S", "E", and "Z" are stereochemical designations familiar to one skilled in the art.

| | |
|---|---|
| Me | methyl |
| Et | ethyl |
| MeOH | methanol |
| EtOH | ethanol |
| i-PrOH | isopropanol |
| Ph | phenyl |
| Bn | benzyl |
| Bu | butyl |
| iBu or i-Bu | isobutyl |
| Pr | propyl |
| iPr or i-Pr | isopropyl |
| t-Bu | tertiary butyl |
| AcOH | acetic acid |
| BINAP | 2,2'-bis(diphenylphosphino)-1,1'-binaphthyl |
| EtOAc | ethyl acetate |
| ADP | adenosine diphosphate |
| 2MeS-ADP | 2 methylthio adenosine diphosphate |
| cDNA | complimentary DNA |
| DCC | dicyclohexylcarbodiimide |
| DCE | 1,2 dichloroethane |
| DCM | dichloromethane |
| DEAD | diethyl azodicarboxylate |
| DIC or DIPCDI | diisopropylcarbodiimide |
| DIEA | diethylpropyl amine |
| DMEM | Dulbecco's modified Eagle media |
| DMF | dimethyl formamide |
| DMSO | dimethyl sulfoxide |
| EDC (or EDC.HCl) or EDCI (or EDCI.HCl) or EDAC | 3-ethyl-3'-(dimethylamino)propyl-carbodiimide hydrochloride (or 1-(3-dimethylaminopropyl)-3-ethyl-carbodiimide hydrochloride) |
| EDTA | ethylenediaminetetraacetic acid |
| FBS | Fetal Bovine Serum |
| HEPES | 4-(2-hydroxyethyl)piperaxine-1-ethanesulfonic acid |
| LDA | lithium diisopropylamide |
| mCPBA or MCPBA | meta-chloroperbenzoic acid |
| OMs | mesylate, methanesulfoate |
| OTf | triflate, trifluoromethanesulfonate |
| OTs | tosylate, para-toluenesulfonate |
| D PBS | Dulbecco's Phosphate Buffered Saline |
| Pd/C | palladium on carbon |
| SCX | Strong Cation Exchanger |
| THF | tetrahydrofuran |
| TFA | trifluoroacetic acid |
| TRIS | tris (hydroxymethyl) aminomethane |

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C. *Comprehensive Organic Transformations*, VCH: New York, 1989. Preferred methods include, but are not limited to, those described below. All references cited herein are hereby incorporated in their entirety herein by reference.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

Schemes 1-6 describe synthetic routes of making compounds of the present invention. Schemes 1-3 describe the preparation of compounds of the present invention from a key amine intermediate 1 whereas Schemes 4-6 describe various preparations of the amines 1.

The synthesis of the compounds of the present invention involves the coupling of the boronic acid derivatives 3 (or boronate, borate) with commercially available or readily prepared by one skilled in the art amino compounds 4 according to the Scheme 1. Depending on the structure and substituents involved, the reaction is carried out with or without micro waves and molecular sieves, at temperatures between 0° C. and 200° C. in an appropriated organic solvent such as $CH_2Cl_2$, in the presence of a base such as pyridine or TEA.

The compounds of the present invention can also be prepared by one of the methods described in the reviewed article Modern Synthetic methods for cooper-mediated C(aryl)-O; C(aryl)-N and C(aryl)-S bond formation by Steven V. Lay and Andrew W. Thomas in *Angew. Chem. Int. Ed.* 2003, 42, 5400-5449. Alternatively other organometalloides such as siloxanes, stannanes or organobismuth reagents can be employed in place of boronic acid derivatives.

The amino derivative 1, is transformed to the corresponding halogen intermediate 2 by well known diazotation reaction. In turn, intermediate 2 is transformed to the boronic acid compound 3 by the classical boronic acid derivatives preparation methods known in the literature (Pd-catalyzed borylation of aryl halides Marshall, J. A. *Chemtracts* 2000, 13(4), 219-222; New methods for the synthesis of proximally functionalized arylboranes and silanes. Katz, H. E. *Organometallics* 1986, 5(11), 2308-11; Palladium-Catalyzed Borylation of Aryl Halides or Triflates with Dialkoxyborane: A Novel and Facile Synthetic Route to Arylboronates. Murata, M. et al. *Journal of Organic Chemistry* 2000, 65(1), 164-168).

Scheme 1

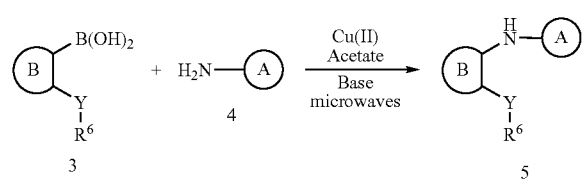

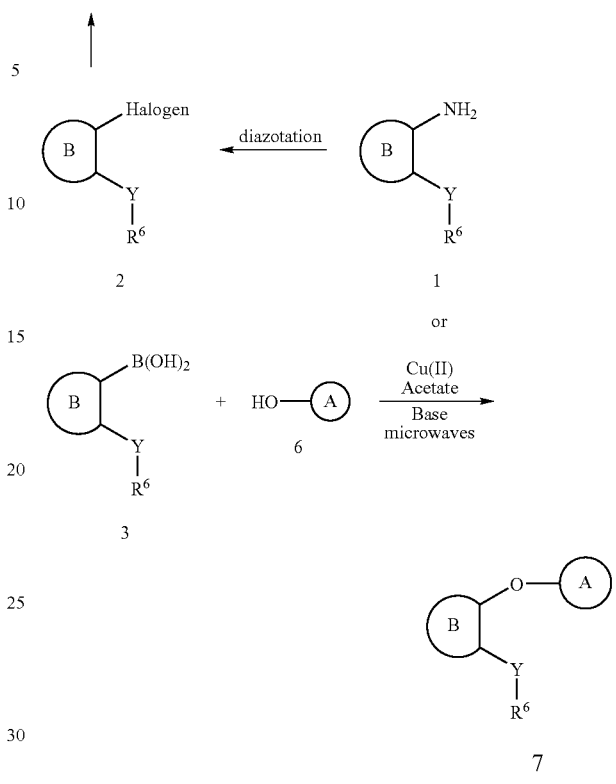

Alternatively, the compounds of the present invention can be prepared using amine 1 and boronic acid 8 under reaction conditions similar to that described above.

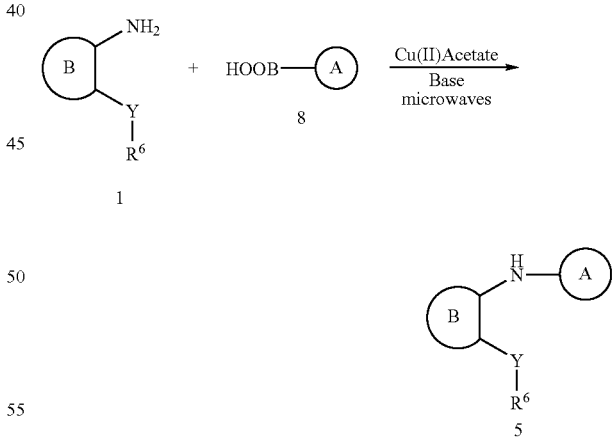

Scheme 3 describes an alternative method to synthesize the compounds of the present invention. In this case the metal catalyzed coupling of the amines with an aryl or heteroaryl halide or triflate is used. A variety of examples of such couplings are provided the following articles and book: Muci, A. R.; Buchwald, S. L. *Top. Curr. Chem.* 2002, 219, 131. and Hartwig, J. F. In Modern Amination Methods; Ricci, A., Ed., Wiley-VCH: Weinheim, Germany, 2000.

Scheme 3

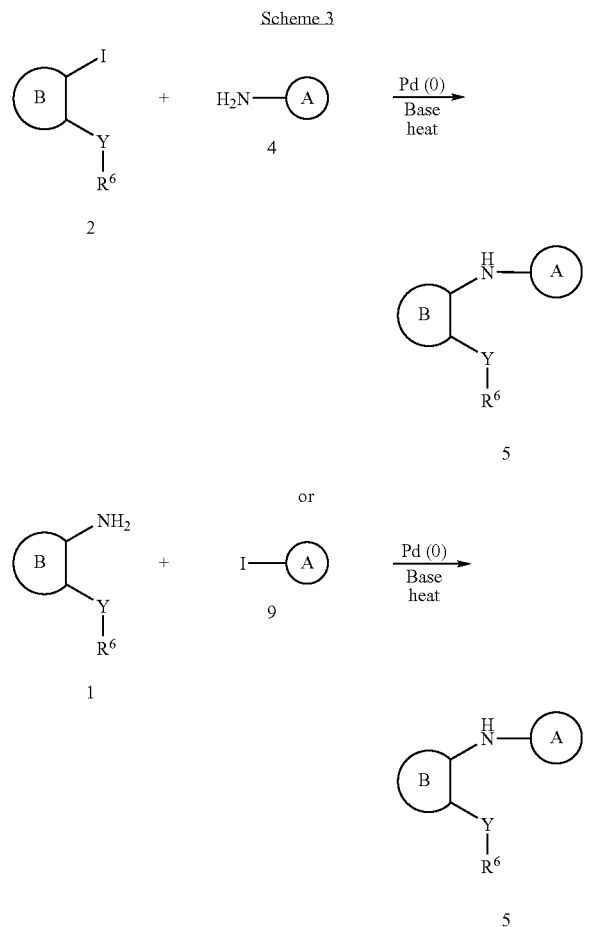

Scheme 4 outlines one possible preparation of amino derivatives 1, which proceeds by aromatic nucleophilic substitution followed by reduction. Nitroaryl derivatives or nitroheteroaryl derivatives 10, substituted in the ortho position with a halogen (such as chlorine, fluorine or bromine), are commercially available or can readily be prepared by one skilled in the art of organic synthesis. They can be reacted with nucleophiles such as substituted alcohols, substituted amines, or substituted thiols to provide the corresponding ether, amine or thioether, respectively. Typical reaction conditions involve the reaction of a nucleophile and a halo nitro derivative in an organic solvent such as THF, DMF, toluene, dioxane or n-butanol, in the presence of a base such as potassium carbonate, cesium carbonate, triethylamine, or DIEA. The reaction temperature is usually between room temperature and reflux condition. Sometimes microwave irradiation can be used to accelerate the rate of reaction. The preferred synthesis of diaryl ethers proceeds by an ortho chloro-nitroaryl derivative with a substituted phenol and cesium carbonate at 80° C. in DMF. Diaryl amines are preferably obtained by reacting an ortho chloro-nitroaryl derivative with a substituted aniline and triethylamine in butanol at 210° C. using microwave irradiation.

Following aromatic nucleophilic substitution, the resulting nitro derivative 12 can be reduced to the corresponding aniline. Typical conditions include hydrogenation in the presence of a metal catalyst such as palladium or platinum. Other conditions include treatment with reducing agents such as $SnCl_2$ or Zinc powder with ammonium chloride.

Scheme 4

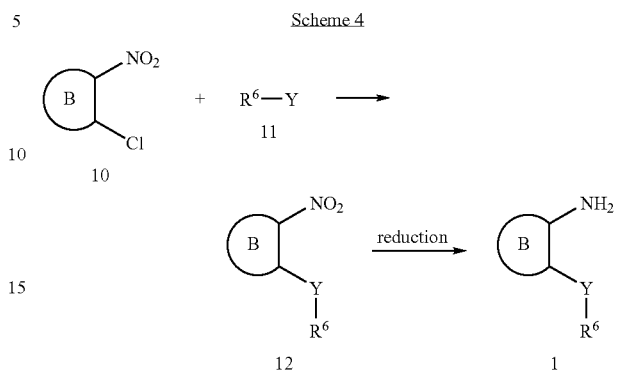

Preparation of substituted pyridine amines such as 14, 15, 16, or 17 is shown in Scheme 5. The pyridine aniline 13 prepared as described in Scheme 4 can be brominated or chlorinated using agents such as N-bromosuccinimide or N-chlorosuccinimide in an organic solvent such as DMF. The resulting aromatic bromide can be converted to the corresponding nitrile by metal catalyzed cyanation. For example, reaction of the bromide 14 (X=Br) with copper (I) cyanide, tris-(dibenzylideneaceteone)-bispalladium, diphenylphosphine ferrocene and tetrabutylammonium cyanide affords the corresponding nitrile 15. The resulting nitrile can be hydrolyzed to the corresponding carboxylic acid using methods know in the art of organic synthesis such as treatment with aqueous sodium hydroxide. Conversion of the corresponding carboxylic acid to the methyl ester can be accomplished by treatment with trimethylsilyl diazomethane or with hydrochloric acid in methanol. Alternatively, the nitrile 15 can be converted to the corresponding ester 16 and amide 17 by acidic or basic hydrolysis.

Scheme 5

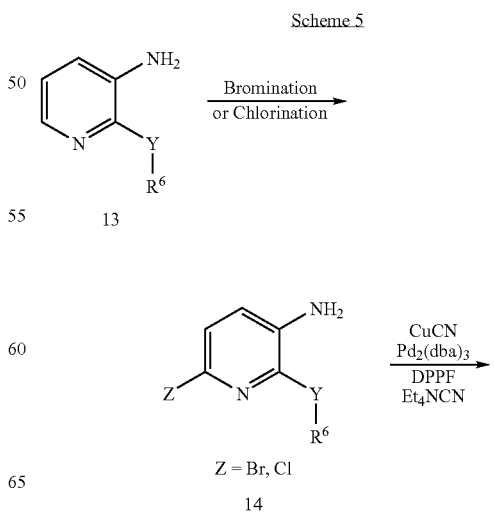

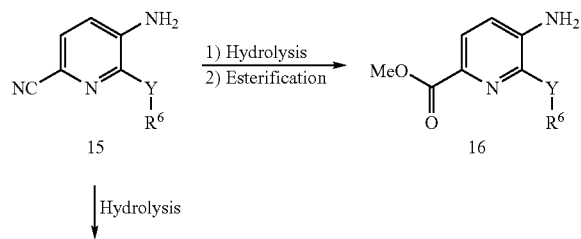

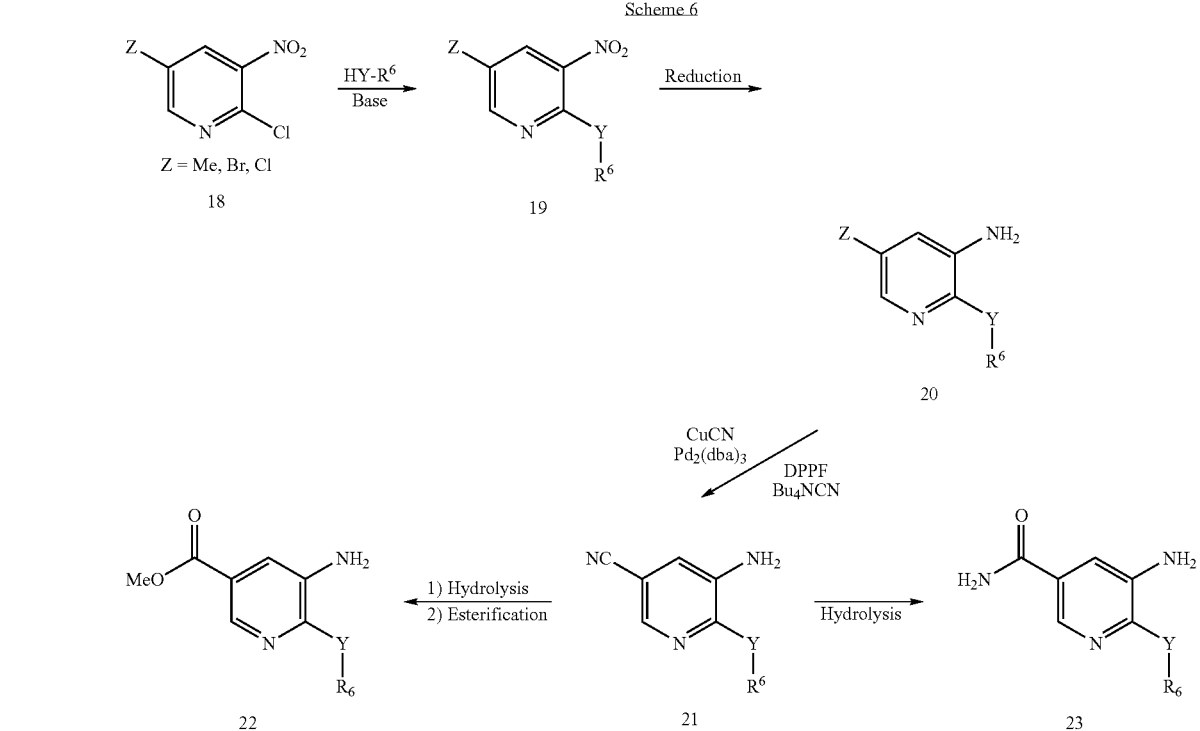

nitrile by metal catalyzed cyanation. For example, reaction of the bromide 20 (Z=Br) with copper (I) cyanide, tris-(dibenzylideneaceteone)-bispalladium, diphenylphosphine ferrocene and tetrabutylammonium cyanide affords the corresponding nitrile 21. The resulting nitrile can be hydrolyzed to the corresponding carboxylic acid using methods know in the art of organic synthesis such as treatment with aqueous sodium hydroxide. Conversion of the corresponding carboxylic acid to the methyl ester 22 can be accomplished by treatment with trimethylsilyl diazomethane or with hydrochloric acid in methanol. Alternatively, the nitrile 21 can be converted to the corresponding amide 23 by acidic or basic hydrolysis.

-continued

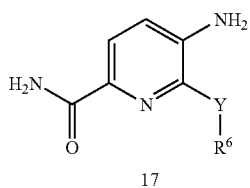

Preparation of substituted pyridine amines such as 20, 21, 22 or 23 is shown in Scheme 6. The nitrochloro pyridine 18 can be prepared as described above for Scheme 4. The resulting aromatic bromide can be converted to the corresponding nitrile by metal catalyzed cyanation.

In the following experimental procedures, solution ratios express a volume relationship, unless stated otherwise. NMR chemical shifts (δ) are reported in parts per million.

Products were analyzed by reverse phase analytical HPLC carried out on a Shimadzu Analytical HPLC system running DiscoveryVP software using Method A: Phenominex Luna C18 column (4.6×50 mm) eluted at 4 mL/min with a 4 min gradient from 100% A to 100% B (A: 10% methanol, 89.9% water, 0.1% TFA; B: 10% water, 89.9% methanol, 0.1% TFA, UV 220 nm), Method B: Phenominex Luna C18 column (4.6×50 mm) eluted at 4 mL/min with a 4 min gradient from 100% A to 100% B (A: 10% acetonitrile, 89.9% water, 0.1% TFA; B: 10% water, 89.9% acetonitrile, 0.1% TFA, UV 220 nm), or Method C: Zorbax SB C18 column (4.6×75 mm) eluted at 2.5 mL/min with methanol/water with 0.2% $H_3PO_4$ as a gradient of 10% to 90% methanol over 8 min followed by holding at 90% methanol for 3 min (UV 220 nm). Purification of intermediates and final products was carried out via either normal or reverse phase chromatography. Normal phase chromatography was carried out on an ISCO CombiFlash™ System Sq16x using prepacked SiO$_2$ cartridges eluted with gradients of hexanes and ethyl acetate. Reverse phase preparative HPLC was carried out using a Shimadzu Preparative HPLC system running DiscoveryVP software on a Shim-PackVP-ODS column (50 L×20 mm) at 20 mL/min, 6 min gradient 100% A to 100% B with the solvent system used for the analytical. LCMS were obtained on a Shimadzu HPLC system running DiscoveryVP software, coupled with a Waters Model PlatformLC mass spectrometer running Mass-Lynx version 3.5 software using the same column and conditions as utilized for analytical described above.

EXAMPLES

The following Examples have been prepared, isolated and characterized using the methods disclosed herein. The following Examples demonstrate a partial scope of the invention and are not meant to limit the scope of the invention.

Intermediate 1

2-(2-tert-butylphenoxy)-3-aminopyridine

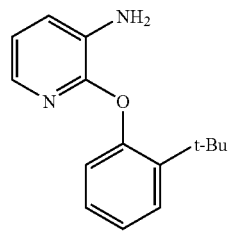

Intermediate 1a. 2-(2-tert-butylphenoxy)-3-nitropyridine: A solution of 2-chloro-3-nitropyridine (21.1 g, 133 mmol) in DMF (100 mL) was treated with 2-tert-butylphenol (23.5 mL, 153 mmol) and cesium carbonate (130 g, 398 mmol). The mixture was heated at 80° C. for 30 h. The reaction was cooled to rt and the mixture was poured into water (1 L) with stirring. The resulting yellow precipitate was filtered, washed with water, and recrystallized from ethanol to afford Intermediate 1a (32.8 g, 90% yield) as beige crystals; HPLC purity: 92%, 3.66 min (Method A); $^1$H NMR (400 MHz, CD$_3$OD) δ ppm 1.34 (s, 9H), 6.93 (m, 1H), 7.22 (m, 3H), 7.47 (m, 1H), 8.31 (dd, J=4.82, 1.75 Hz, 1H), 8.46 (dd, J=7.89, 1.75 Hz, 1H).

Intermediate 1: Intermediate 1a (7.2 g, 27 mmol) was dissolved in a 1:1 mixture of methanol and ethyl acetate (160 mL). Palladium on charcoal (10%, 360 mg, 0.33 mmol) was added and the mixture was stirred overnight under hydrogen atmosphere (40 psi). The reaction mixture was filtered over Celite® and concentrated to afford Intermediate 1 (7.2 g, 100% yield) as a white powder; HPLC purity: 100%, 2.87 min (Method A); [M+H]$^+$=243.3.

Intermediate 2

2-(3-tert-butylphenoxy)pyridin-3-amine

Intermediate 2 was prepared according to the procedure described above for Intermediate 1 using 3-tert-butylphenol instead of 2-tert-butylphenol.

Example 1 methyl 3-(2-(2-tert-butylphenoxy)pyridin-3-ylamino)benzoate

To a solution of Intermediate 1 (100 mg, 0.414 mmol) in 1,2-dichloroethane (4 mL) in a 25 mL scintillation vial under air was added 3-(methoxycarbonyl)phenylboronic acid (148 mg, 0.818 mmol), triethylamine (120 µL), pyridine (120 µL), powdered 4 Å sieves (150 mg) and lastly Cu(OAc)$_2$ (51 mg, 0.28 mmol). The reaction was stirred overnight (~16 h) at rt. The reaction was filtered through a 40 µm filter and solvent removed. Purification by flash chromatography (40 g ISCO silica gel cartridge, 0-15% Ether/Hexane) provided Example 1 (93 mg). (M+H)+=377.34. $^1$H NMR (400 MHz, CD$_3$OD) δ ppm 1.31 (s, 9H), 3.87 (s, 3H), 6.92 (dd, J=8.14, 1.76 Hz, 1H), 7.01 (dd, J=7.92, 4.84 Hz, 1H), 7.11 (td, J=7.92, 1.32 Hz, 1H), 7.19 (m, 1H), 7.34 (m, 2H), 7.42 (dd, J=7.92, 1.76 Hz, 1H), 7.54 (m, 1H), 7.61 (dd, J=4.84, 1.32 Hz, 1H), 7.66 (dd, J=7.92, 1.76 Hz, 1H), 7.73 (dd, J=2.16, 1.76 Hz, 1H); $^{13}$C NMR (400 MHz, CD$_3$OD) δ ppm 30.9, 35.5, 52.6, 119.6, 120.1, 123.0, 123.8, 124.2, 125.6, 126.9, 128.0, 128.3, 130.4, 130.5, 132.3, 139.0, 142.7, 144.9, 154.1, 156.1, 168.7.

Example 2

2-(2-tert-butylphenoxy)-N-phenylpyridin-3-amine

A solution of BINAP (42 mg, 0.067 mmol) and Pd(OAc)$_2$ (10 mg, 0.044 mmol) in nitrogen degassed toluene (10 mL) was degassed for 10 min. A portion of this solution (1 mL) was added to a 1 dram vial containing Intermediate 1 (30 mg, 0.12 mmol), phenyl bromide (25 mg, 0.16 mmol) and Cs$_2$CO$_3$ (80 mg, 0.246 mmol). The reaction mixture was degassed for 5 min. with nitrogen, sealed and heated to 100° C. overnight (~18 h). Purification by preparative HPLC (C18 28 mm×100 mm, 20-100% solvent B, 10 min. gradient, 4 min. hold, 25 ml/min: solvent A=10% MeOH/Water+0.1% TFA, solvent B=90% MeOH/Water+0.1% TFA) provided Example 2 (32.7, 0.10 mmol). (M+H)$^+$=319.32

Example 5

Methyl 3-(2-(2-tert-butylphenoxy)pyridin-3-yloxy)benzoate 5a. 2-(2-tert-Butylphenoxy)-3-iodopyridine: To a solution of 2-(2-tert-butylphenoxy)-3-aminopyridine (3.30 g, 13.6 mmol) in conc. HCl:water (3:4, 70 mL) at 0° C. was added NaNO$_2$ (1.04 g, 15.0 mmol). Gas evolution was immediately observed. The reaction was stirred at 0° C. for 25 min. and then the reaction was slowly poured into a rt solution of KI (6.8, 40.8 mmol) in water (150 mL) to produce a dark liquid containing an amount of a black. After heating the reaction at 60° C. for 2 h, the reaction was cooled to rt and extracted with ethyl acetate (2×200 mL). The combined ethyl acetate extracts were then washed with saturated aqueous Na$_2$SO$_3$ (2×300 mL) and saturated aqueous Na$_2$CO$_3$ (1×300 mL). The ethyl acetate extracts were then dried over MgSO$_4$, filtered and concentrated. Purification of the residue by flash chromatography—(110 g ISCO silica gel column, 0 to 5% EtOAc in hexane step gradient)—gave 5a (3.35 g) as a pale yellow solid. $^1$H NMR (400 MHz, CDCl$_3$) δ ppm 1.39 (s, 9H); 6.74 (dd, J=7.47, 4.83 Hz, 1H); 6.93 (dd, J=7.91, 1.32 Hz, 1H); 7.12-7.25 (m, 2H); 7.45 (dd, J=7.91, 1.76 Hz, 1H); 8.10 (dd, J=4.83, 1.76 Hz, 1H); 8.15 (dd, J=7.69, 1.54 Hz, 1H).

5b. 2-(2-tert-Butylphenoxy)-pyridine-3-boronic acid: To a solution of Example 5a (3.35 g, 9.49 mmol) in THF (60 mL) under nitrogen at −78° C. was added 2.0 M nBuLi in pentane (14.2 mL, 28.47 mmol, 3 eq) over ~3 min. The reaction was stirred at −78° C. for 10 min & then B(OiPr)$_3$ (6.54 mL, 28.47 mmol, 3 eq) was added in a single aliquot. The reaction was stirred at −78° C. for 40 min & then the reaction was poured into water (~60 mL) followed by the addition of LiOH (~3.5 g). The reaction was stirred for 2 h at rt. The reaction mixture was partitioned between water (~200 ml additional) and EtOAc (~200 mL), and layers were separated. The aqueous layer was washed once more with EtOAc and poured into a large erlenmyer flask and was added more EtOAc (~200 mL). With vigorous stirring, conc. HCl was added to the aqueous layer dropwise until pH ~2. Layers were separated in sep. funnel and aqueous layer was extracted once more with EtOAc (~200 mL). These last two EtOAc extracts were combined, dried over sodium sulfate, filtered and concentrated, then azeotroped twice with toluene to give 5b (2.38 g) as a white solid. $^1$H NMR (400 MHz, CDCl$_3$) δ ppm 1.31 (s, 9H); 4.1 (bs, 1H); 5.61 (bs, 1H); 6.91 (d, J=7.47 Hz, 1H); 7.05 (dd, J=6.37, 3.74 Hz, 1H); 7.15-7.3 (m, 2H); 7.48 (dd, J=7.47, 1.32 Hz, 1H); 8.23 (bs, 1H); 8.27 (dd, J=7.03 Hz, 1H).

Example 5

To a solution of Example 5b (11 mg, 0.0406 mmol) in dichloromethane (1.5 mL) in a scintillation vial under air at rt was added methyl 3-hydroxybenzoate (25 mg, 0.164), powdered 4 Å molecular sieves (~150 mg), Et$_3$N (60 µL), pyridine (60 µL) and lastly Cu(OAc)$_2$ (15 mg, 0.0828 mmol). The reaction vessel was capped and the reaction was stirred at rt overnight. The reaction mixture was diluted with hexane (2.5 mL), and filtered through a 40 µm filter. Solvents were reduced and the residue was loaded to a silica gel column and purified by flash chromatography (0-10% EtOAc in hexane, step gradient) to provide Example 5 (1.49 mg) as a tan solid. (M+H)$^+$=378.21.

Example 6

2-(2-tert-butylphenoxy)-N-(naphthalen-1-yl)pyridin-3-amine

The experimental procedure described for Example 7 below was applied to naphthalen-1-amine to yield compound of Example 6. t$_R$=8.461 min (Shimadzu Phenomenex S5 ODS 4.6×50 mm Luna 4.6×50 mm; flow rate 2.5 mL/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{25}$H$_{25}$N$_2$O [M+H]$^+$369.1967, found 369.1953. $^1$H NMR (400 MHz, MeOD) δ ppm 1.42 (s, 9H), 6.88 (dd, J$_1$=7.5 Hz, J$_2$=4.8 Hz, 1H), 7.02 (dd, J$_1$=7.9 Hz, J$_2$=1.3 Hz, 1H), 7.07 (dd, J=7.9 Hz, J$_2$=1.8 Hz, 1H), 7.16 (m, 1H), 7.26 (m, 1H), 7.40 (dd, J$_1$=6.1 Hz, J$_2$=1.3 Hz, 1H), 7.49 (m, 5H), 7.70 (d, J=7.9 Hz, 1H), 7.91 (dd, J=7.9 Hz, 1H), 8.00 (dd, J=8.0 Hz, 1H).

Example 7

2-(2-tert-butylphenoxy)-N-(naphthalen-2-yl)pyridin-3-amine

To a solution of naphthalen-2-amine (143.2 mg, 1 mmol), in dichloromethane (2.5 mL) in a scintillation vial were added 271.13 mg (1 mmol) of the boronic acid 5b prepared as above. Subsequently, 250 µL of TEA was added and finally 181.64 mg (1 mmol) of Cu(OAc)$_2$ was introduced and the vessel was capped. The reaction mixture was microwaved at 100° C. for 30 min (Personal chemistry; Emrys Optimizer from Biotage). The dark suspension was filtered through Celite® 454 and Example 7 was isolated after two successive preparative HPLC. t$_R$=8.311 min (Shimadzu Phenomenex S5 ODS 4.6×50 mm Luna 4.6×50 mm; flow rate 2.5 mL/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{25}$H$_{25}$N$_2$O [M+H]$^+$369.1967, found 369.1966. $^1$H NMR (400 MHz, MeOD) δ ppm 1.36 (s, 9H), 6.97 (dd, J=7.9 Hz, J$_2$=1.3 Hz, 1H), 7.04 (Q, J=7.9 Hz, 1H), 7.15 (m, 1H), 7.23 (m, 1H), 7.31 (m, 1H), 7.39 (m, 2H), 7.46 (dd, J=7.9 Hz, J$_2$=1.4 Hz, 1H), 7.53 (d, J=1.8 Hz, 1H), 7.57 (dd, J$_1$=3.5 Hz, J$_2$=1.4 Hz), 7.69 (d, J=8.2 Hz, 1H), 7.76 (d, J=7.9 Hz, 1H), 7.80 (m, 2H).

Example 9

2-(2-tert-butylphenoxy)-N-(2,3-dihydro-1H-inden-5-yl)pyridin-3-amine

A mixture of 5a (148 mg, 0.42 mmol), 5-amino indane (62 mg, 0.47 mmol), dppf (7.0 mg, 0.013 mmol), Pd$_2$(dba)$_3$ (7.7 mg, 0.008 mmol), sodium tert-butoxide (61 mg, 0.64 mmol) in toluene (2.0 mL) was heated in a seal tube at 110° C. for 32 h. The mixture was allowed to cool and saturated ammonium chloride (30 mL) was added and the mixture was extracted with ethyl acetate (3×25 mL). The combined organic layers were dried (anhydrous sodium sulfate), filtered and evaporated to yield a residue was purified by reverse phase preparative HPLC to provide Example 9. (M+H)$^+$=359; $^1$H NMR (400 MHz, DMSO-d$_6$) δ ppm 1.31 (s, 9 H), 2.00 (m, 2H), 2.80 (m, 4H), 6.91 (dd, J=8.0, 1.3 Hz, 1H), 6.93-6.97 (m, 2H), 7.06 (s, 1H), 7.10-7.13 (m, 2H), 7.22 (td, J=7.6, 1.6 Hz, 1H), 7.39 (dd, J=8.0, 1.6 Hz, 1H), 7.50-7.54 (m, 2H), 7.64 (s, 1H).

Additional examples were prepared in similar procedures as described above. Table 1 below summarizes representative examples of the compounds in the present invention.

TABLE 1

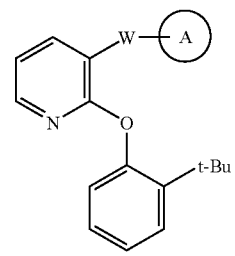

| Ex | W | R⁶ | ring A | Chemical Name | MS data (M + H) |
|---|---|---|---|---|---|
| 1 | NH | 2-t-Bu-Ph | 3-CO$_2$Me-Ph | methyl 3-(2-(2-tert-butylphenoxy)pyridin-3-ylamino)benzoate | 377.3 |
| 2 | NH | 2-t-Bu-Ph | Ph | 2-(2-tert-butylphenoxy)-N-phenylpyridin-3-amine | 319.3 |
| 3 | NH | 2-t-Bu-Ph | 4-OBn-Ph | N-(4-(benzyloxy)phenyl)-2-(2-tert-butylphenoxy)pyridin-3-amine | 425.29 |
| 4 | NH | 2-t-Bu-Ph | 4-CO$_2$Me-Ph | methyl 4-(2-(2-tert-butylphenoxy)pyridin-3-ylamino)benzoate | 377.3 |
| 5 | O | 2-t-Bu-Ph | 3-CO$_2$Me-Ph | methyl 3-(2-(2-tert-butylphenoxy)pyridin-3-yloxy)benzoate | 378.3 |
| 6 | NH | 2-t-Bu-Ph | 1-naphthyl | 2-(2-tert-butylphenoxy)-N-(naphthalen-1-yl)pyridin-3-amine | 369.19 |
| 7 | NH | 2-t-Bu-Ph | 2-naphthyl | 2-(2-tert-butylphenoxy)-N-(naphthalen-2-yl)pyridin-3-amine | 369.19 |
| 8 | NH | 3-t-Bu-Ph | indanyl | 2-(3-tert-butylphenoxy)-N-(2,3-dihydro-1H-inden-5-yl)pyridin-3-amine | 359 |
| 9 | NH | 2-t-Bu-Ph | indanyl | 2-(2-tert-butylphenoxy)-N-(2,3-dihydro-1H-inden-5-yl)pyridin-3-amine | 359 |

Utility

The compounds of the present invention are anti-platelet agents and thus are useful to maintain the fluidity of blood. Additionally, compounds of the present invention are useful for the treatment or prophylaxis of platelet-associated disorders. As used herein, the term "platelet-associated disorder" refers to any disorder which may be prevented, partially alleviated, or cured by the administration of an anti-platelet agent.

The term anti-platelet agents (or platelet inhibitory agents), as used herein, denotes agents that inhibit platelet function, for example, by inhibiting the aggregation, adhesion or granule content secretion of platelets.

The term "thrombosis", as used herein, refers to formation or presence of a thrombus (pl. thrombi); clotting within a blood vessel which may cause ischemia or infarction of tissues supplied by the vessel. The term "embolism", as used herein, refers to sudden blocking of an artery by a clot or foreign material which has been brought to its site of lodgment by the blood current. The term "thromboembolism", as used herein, refers to obstruction of a blood vessel with thrombotic material carried by the blood stream from the site of origin to plug another vessel.

In general, a thromboembolic disorder is a circulatory disease caused by blood clots (i.e., diseases involving fibrin formation, platelet activation, and/or platelet aggregation). The term "thromboembolic disorders (or conditions)" as used herein also includes arterial or venous cardiovascular or cerebovascular thromboembolic disorders, and thromboembolic disorders in the chambers of the heart or in the peripheral circulation.

Thus, the compounds of the present invention are useful in the treatment or prevention of various platelet associated disorders including: thrombotic or thromboembolic conditions; acute coronary syndromes (such as coronary artery disease, myocardial infarction (MI), unstable angina, and non-Q Wave MI); thromboembolic stroke (such as that resulting from atrial fibrillation or from ventricular mural thrombus (low ejection fraction)); venous thrombosis (including deep vein thrombosis); arterial thrombosis; cerebral thrombosis; pulmonary embolism; cerebral embolism; kidney embolisms; peripheral occlusive arterial disease (e.g., peripheral arterial disease, intermittent claudication, critical leg ischemia, prevention of amputation, prevention of cardiovascular morbidity such as MI, transient ischemic attack, stroke, or ischemic sudden death); thromboembolic consequences of surgery, interventional cardiology or immobility; thromboembolic consequences of medication (such as oral contraceptives, hormone replacement, and heparin); thrombotic consequences of atherosclerotic vascular disease and atherosclerotic plaque rupture leading to tissue ischemia; prevention of atherosclerotic plaque formation; transplant atherosclerosis; thromboembolic complications of pregnancy including fetal loss; thromboembolic consequences of thrombophilia (e.g., Factor V Leiden, and homocystinenimia); prothrombotic consequences and/or complications of cancer; coagulopathies (e.g., disseminated intravascular coagulation (DIC)); coagulation syndromes; vascular remodeling atherosclerosis, restenosis and systemic infection; prevention of metastasis and tumor implantation; diabetic complications including retinopathy, nephropathy and neuropathy; inflammation (e.g., thrombophlebitis); ischemia (such as that resulting from vascular occlusion, cerebral infarction, transient ischemic attack, stroke and related cerebral vascular diseases); Kasabach-Merritt syndrome; atrial fibrillation; ventricular enlargement (including dilated cardiac myopathy and heart failure); restenosis (e.g., following arterial injury-induced either endogenously or exogenously); thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, and vessel grafts. The procedures include, but are not limited to: cardiopulmonary bypass, percutaneous coronary intervention, and hemodialysis.

In addition to acting as anti-platelet agents, the compounds of the present invention may also find utility in a variety of other settings including as inhibitors of bone resorption such as encountered in various osteoporotic conditions, as inhibitors of insulin secretion in conditions of hyperinsulinemia, as vasoconstrictive agents such as those used in cases of septic or hypovolemic shock, as inhibitors of smooth muscle relaxation such for the treatment of incontinence or in other cases where inhibition of sympathetic nerve transmission would be of therapeutic benefit such as nociception or neuronal tissue regeneration. These and many other potential utilities for P2Y$_1$ antagonists have been recently reviewed (Burnstock, G. and Williams, M. *J. Pharm. Exp Ther.* 2000, 295, 862-9) and are suggested therein.

Compounds of the present invention may additionally be useful as diagnostic agents and adjuncts. For example, the present compounds may be useful in maintaining the reactivity of fractionated whole blood containing platelets such as required for analytical and biological testing or transfusions. In addition, the compounds of the present invention may be useful for maintaining blood vessel patency in conjunction with vascular surgery including bypass grafting, arterial reconstruction, atherectomy, vascular graft and stent patency, organ, tissue and cell implantation and transplantation. In addition, the compounds of the present invention may be useful for maintaining blood vessel patency in conjunction with interventional cardiology or vascular surgery including bypass grafting, arterial reconstruction, atherectomy, vascular graft and stent patency, organ, tissue and cell implantation and transplantation.

P2Y$_1$ Assays

A. Binding Assay

A membrane binding assay was used to identify inhibitors of [$^{33}$P] 2MeS-ADP binding to cloned human P2Y$_1$ receptors. The cDNA clone for human P2Y$_1$ was obtained from Incyte Pharmaceuticals and its sequence confirmed by established techniques (for a compendium of techniques used see Ausubel, F. et al. *Current Protocols in Molecular Biology* 1995 John Wiley and Sons, NY, N.Y.). The essential coding sequences were subcloned into pCDNA 3.1 (Invitrogen) to produce a P2Y$_1$ expression construct. This construct was then transfected into the human embryonic kidney cell line HEK-293 and stable transfectants selected in Genetcin® (G418 sulfate; Life Technologies). Several lines were screened for binding activity and one (HEK293 #49) selected for further characterization. Membranes-were prepared by growing HEK293 #49 in 150 mm dishes in DMEM/10% FBS in the presence of 1 mg/ml G418 until cells were 80-90% confluent. Plates were then washed with cold (4° C.) D-PBS twice and cells harvested by scraping into 10 mL D-PBS. Cells were pelleted by centrifugation (1,000 g, 10 min, 4° C.) and the resulting pellet resuspended in Lysis Buffer (10 mM Tris (7.4), 5 mM MgCl$_2$ containing Complete protease inhibitor cocktail (Roche Cat #1873580) as recommended by the manufacturer). The suspension was then homogenized in a Dounce homogenizer (10-15 strokes; B pestle, on ice) and the homogenate spun at 1,000 g, 4° C., 5 min to pellet large debris. The supernatant was centrifuged at 150,000 g, 4° C., for 1 hour and the resulting membrane pellet resuspended in 0.5-1 mL of Buffer B (15 mM HEPES (7.4), 145 mM NaCl, 0.1 mM MgCl$_2$, 5 mM EDTA, 5 mM KCl) and stored at −70° C. until used.

Binding reactions were performed in WGA FlashPlates (PerkinElmer Life Sciences, Cat # SMP105A) in a volume of 200 μL containing ~45 fmol of P2Y$_1$ receptor (5 μg of total protein), 0.5 nM [$^{33}$P] 2MeS-ADP (PerkinElmer; 2,000 Ci/mmol), and various concentrations of the test compound (usually between 50 μM and 10 pM) in Buffer B containing 1% DMSO. Reactions were allowed to proceed to completion at room temperature for 1 hour and then the aqueous solution aspirated. Plates were sealed and the residual [$^{33}$P] bound to the plate determined by scintillation counting. Dose-response curves (IC$_{50}$) were fit by non-linear regression (XLFit, ID Business Solutions Ltd.) and binding constants (K$_i$) calculated using the Cheng-Prusoff relationship (K$_i$=IC$_{50}$/(1+L/K$_d$) in which a K$_d$ for 2MeS-ADP to the P2Y$_1$ receptor was determined to be 1.4 nM.

In general, preferred compounds of the present invention, such as the particular compounds disclosed in the above examples, have been identified to exhibit K$_i$'s of equal to or less than 10 μM in the P2Y$_1$ binding assay, thereby demonstrating these preferred compounds of the present invention as especially effective modulators of P2Y$_1$ activity. More preferred compounds have K$_i$'s of equal to or less than 5 μM, preferably equal to or less than 1 μM, more preferably equal to or less than 0.5 μM.

The effectiveness of compounds of the present invention as antithrombotic agents can be determined using relevant in vivo thrombosis models, including In Vivo Electrically-induced Carotid Artery Thrombosis Models and In Vivo Rabbit Arterio-venous Shunt Thrombosis Models.

In Vivo Electrically-Induced Carotid Artery Thrombosis (ECAT) Model:

The rabbit ECAT model, described by Wong et al. (*J Pharmacol Exp Ther* 2000, 295, 212-218), can be used in this study. Male New Zealand White rabbits are anesthetized with ketamine (50 mg/kg+50 mg/kg/h IM) and xylazine (10 mg/kg+mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to the initiation of thrombosis. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid $E_{max}$ equation (DeltaGraph; SPSS Inc., Chicago, Ill.).

In Vivo Rabbit Arterio-Venous (AV) Shunt Thrombosis Model:

The rabbit AV shunt model, described by Wong et al. (Wong, P. C. et al. *J Pharmacol Exp Ther* 2000, 292, 351-357), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm). The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by a nonlinear least square regression program using the Hill sigmoid $E_{max}$ equation (DeltaGraph; SPSS Inc., Chicago, Ill.).

The compounds of the present invention can be administered alone or in combination with one or more additional therapeutic agents. These other agents include, but are not limited to, anticoagulant or coagulation inhibitory agents, other antiplatelet or platelet inhibitory agents, or thrombolytic or fibrinolytic agents.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Examples of suitable anti-arrhythmic agents for use in combination with the present compounds include: Class I agents (such as propafenone); Class II agents (such as carvadiol and propranolol); Class III agents (such as sotalol, dofetilide, amiodarone, azimilide, and ibutilide); Class IV agents (such as ditiazem and verapamil); $K^+$ channel openers such as $I_{Ach}$ inhibitors, and $I_{Kur}$ inhibitors (e.g., compounds such as those disclosed in WO01/40231).

Examples of suitable antihypertensive agents for use in combination with the compounds of the present invention include: alpha adrenergic blockers; beta adrenergic blockers; calcium channel blockers (e.g. diltiazem, verapamil, nifedipine, amlodipine, and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; angiotensin-converting enzyme (ACE) inhibitors (e.g., captopril, zofenopril, fosinopril, enalapril, ceranopril, cilazopril, delapril, pentopril, quinapril, ramipril, lisinopril); angiotensin AT-1 receptor antagonists (e.g., losartan, irbesartan, valsartan); ET-A receptor antagonists (e.g., sitaxsentan, atrsentan, and compounds disclosed in U.S. Pat. Nos. 5,612,359 and 6,043,265); Dual ET-A/AT-1 antagonist (e.g., compounds disclosed in WO 00/01389); neutral endopeptidase (NEP) inhibitors; vasopepsidase inhibitors (dual NEP-ACE inhibitors) (e.g., omapatrilat, gemopatrilat, and nitrates); and β-blockers (e.g., propanolol, nadolo, or carvedilol).

Examples of other suitable anti-platelet agents for use in combination with the compounds of the present invention, include, but are not limited to, the various known non-steroidal anti-inflammatory drugs (NSAIDS) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDS, aspirin (acetylsalicyclic acid or ASA) and piroxicam are preferred. Other suitable platelet inhibitory agents include glycoprotein IIb/IIIa blockers (e.g., abciximab, eptifibatide, tirofiban, integrelin), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), protease-activated receptor 1 (PAR-1) antagonists (e.g., SCH-530348, SCH-203099, SCH-529153, and SCH-205831), and pharmaceutically acceptable salts or prodrugs thereof.

Other examples of suitable anti-platelet agents for use in combination with the compounds of the present invention, with or without aspirin, include: ADP (adenosine diphosphate) receptor antagonists including $P_2Y_{12}$ antagonists and other $P_2Y_1$ antagonists. Preferred $P_2Y_{12}$ receptor antagonists, but are not limited to, clopidogrel, ticlopidine, prasugrel, and AZD-6140, including pharmaceutically acceptable salts or prodrugs thereof. Ticlopidine and clopidogrel are also preferred compounds since they are known to be more gentle than aspirin on the gastrointestinal tract in use. Clopidogrel is an even more preferred agent.

Examples of suitable anticoagulants for use in combination with the compounds of the present invention include warfarin and heparin (either unfractionated heparin such as enoxaparin and dalteparin or any commercially available low molecular weight heparin, for example LOVENOX™), synthetic pentasaccharide, direct acting thrombin inhibitors including hirudin and argatroban, factor VIIa inhibitors, factor IXa inhibitors, factor Xa inhibitors (e.g., Arixtram, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors IXa, Xa, and XIa, PAI-1 inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable calcium channel blockers (L-type or T-type) for use in combination with the compounds of the present invention include diltiazem, verapamil, nifedipine, amlodipine and mybefradil.

Examples of suitable cardiac glycosides for use in combination with the compounds of the present invention include digitalis and ouabain.

Examples of suitable diruetics for use in combination with the compounds of the present invention include: chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone.

Examples of suitable mineralocorticoid receptor antagonists for use in combination with the compounds of the present invention include sprionolactone and eplirinone.

Examples of suitable cholesterol/lipid lowering agents and lipid profile therapies for use in combination with the compounds of the present invention include: HMG-CoA reductase inhibitors (e.g., pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; nicotonic acid; fenofibric acid derivatives (e.g., gemfibrozil, clofibrat, fenofibrate and benzafibrate); probucol; cholesterol absorption inhibitors; and cholesterol ester transfer protein inhibitors (e.g., CP-529414).

Examples of suitable anti-diabetic agents for use in combination with the compounds of the present invention include: biguanides (e.g. metformin); glucosidase inhibitors (e.g. acarbose); insulins (including insulin secretagogues or insulin sensitizers); meglitinides (e.g. repaglinide); sulfonylureas (e.g., glimepiride, glyburide and glipizide); biguanide/glyburide combinations (e.g., glucovance), thiozolidinediones (e.g. troglitazone, rosiglitazone, and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DPP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protein tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., conjugated estrogens) and estradiol.

Examples of suitable anti-obesity agents for use in combination with the compounds of the present invention include orlistat, aP2 inhibitors (such as those disclosed in WO00/59506), and cannabinoid receptor CB1 antagonists (e.g., rimonabant, AVE-1625, SR-147778, and CP-945598).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each. A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of platelet ADP receptor. Such compounds may be provided in a commercial kit, for example, for use in pharmaceutical research involving platelet ADP receptor. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving platelet ADP receptor. For example, the presence of $P2Y_1$ in an unknown sample could be determined by addition of the relevant radiolabled compound to the sample and measuring the extend of binding to the $P2Y_1$ receptor.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 0.1 to 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to 100 milligrams of the compound of the present invention and about 0.1 to 7.5 milligrams of the second anticoagulant, per kilogram of patient body weight. For a tablet dosage form, the compounds of this invention generally may be present in an amount of about 5 to 100 milligrams per dosage unit, and the second anti-coagulant in an amount of about 1 to 50 milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolytic agent when administered alone may be reduced by about 50-80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

What is claimed is:

1. A compound of Formula (I):

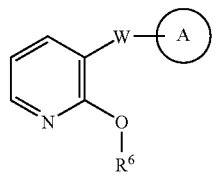

or a stereoisomer, a tautomer, or a pharmaceutically acceptable salt thereof, wherein:
ring A is phenyl substituted with 0-4 $R^1$, 1,2-dihydroinden-6-yl, 1-naphthyl, or 2-naphthyl;
$R^1$ is, independently at each occurrence, F, Cl, Br, I, $CF_3$, $-CF_2CF_3$, $OCF_3$, $-OCF_2CF_2H$, $-OCF_2CF_3$, CN, $NO_2$, $CO_2H$, $CO_2(C_{1-4}$ alkyl), or $C_{1-8}$ alkyl;
W is NH or O;
$R^6$ is phenyl substituted with 0-3 $R^{6a}$; and
$R^{6a}$ is, independently at each occurrence, F, Cl, Br, I, CN, $CF_3$, $OCF_3$, $C_{1-4}$ haloalkyl, $C_{1-4}$ haloalkyloxy-, $C_{1-4}$ alkyloxy-, $C_{1-4}$ alkylthio-, $C_1$-$C_4$ alkyl-C(O)—, $C_{1-4}$ alkyl-O—C(O)—, $C_{1-4}$ alkyl-C(O)NH—, $C_{1-8}$ alkyl, $C_{2-8}$ alkenyl, or $C_{2-8}$ alkynyl.

2. A compound according to claim 1, wherein:
ring A is Ph, 3-$CO_2$Me-Ph, 4-$CO_2$Me-Ph, 4-OBn-Ph, 1,2-dihydroinden-6-yl, 1-naphthyl, or 2-naphthyl; and
$R^6$ is 2-t-Bu-Ph, or 3-t-Bu-Ph.

3. A compound according to claim 1, wherein the compound is selected from the group consisting of:
methyl 3-(2-(2-tert-butylphenoxy)pyridin-3-ylamino)benzoate;
2-(2-tert-butylphenoxy)-N-phenylpyridin-3-amine;
N-(4-(benzyloxy)phenyl)-2-(2-tert-butylphenoxy)pyridin-3-amine;
methyl 4-(2-(2-tert-butylphenoxy)pyridin-3-ylamino)benzoate;
methyl 3-(2-(2-tert-butylphenoxy)pyridin-3-yloxy)benzoate;
2-(2-tert-butylphenoxy)-N-(naphthalen-1-yl)pyridin-3-amine;
2-(2-tert-butylphenoxy)-N-(naphthalen-2-yl)pyridin-3-amine;
2-(3-tert-butylphenoxy)-N-(2,3-dihydro-1H-inden-5-yl)pyridin-3-amine; and
2-(2-tert-butylphenoxy)-N-(2,3-dihydro-1H-inden-5-yl)pyridin-3-amine;
or a pharmaceutically acceptable salt thereof.

4. A pharmaceutical composition, comprising: a pharmaceutically acceptable carrier and a therapeutically effective amount of a compound of claim 1.

5. A pharmaceutical composition, comprising: a pharmaceutically acceptable carrier and a therapeutically effective amount of a compound of claim 2.

6. A pharmaceutical composition, comprising: a pharmaceutically acceptable carrier and a therapeutically effective amount of a compound of claim 3.

* * * * *